United States Patent
Kida et al.

(10) Patent No.: US 11,186,821 B2
(45) Date of Patent: Nov. 30, 2021

(54) METHOD FOR INDUCING DIFFERENTIATION OF NEURAL CREST CELLS INTO NEURONS OF THE AUTONOMIC NERVOUS SYSTEM

(71) Applicant: National Institute of Advanced Industrial Science and Technology, Tokyo (JP)

(72) Inventors: Yasuyuki Kida, Tsukuba (JP); Yuzo Takayama, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 203 days.

(21) Appl. No.: 15/578,454

(22) PCT Filed: Apr. 26, 2016

(86) PCT No.: PCT/JP2016/063006
§ 371 (c)(1),
(2) Date: Nov. 30, 2017

(87) PCT Pub. No.: WO2016/194522
PCT Pub. Date: Dec. 8, 2016

(65) Prior Publication Data
US 2018/0155682 A1    Jun. 7, 2018

(30) Foreign Application Priority Data
Jun. 2, 2015 (JP) .............................. JP2015-112237

(51) Int. Cl.
*C12N 5/00* (2006.01)
*C12N 5/0793* (2010.01)
*C12N 1/00* (2006.01)

(52) U.S. Cl.
CPC ............. *C12N 5/0619* (2013.01); *C12N 1/00* (2013.01); *C12N 5/00* (2013.01); *C12N 2501/155* (2013.01); *C12N 2501/30* (2013.01); *C12N 2501/41* (2013.01); *C12N 2501/415* (2013.01); *C12N 2501/48* (2013.01); *C12N 2506/03* (2013.01)

(58) Field of Classification Search
None
See application file for complete search history.

(56) References Cited

U.S. PATENT DOCUMENTS

2015/0299652 A1* 10/2015 Guo .................. C12N 5/062
424/93.7

FOREIGN PATENT DOCUMENTS

WO    98/48001    10/1998

OTHER PUBLICATIONS

Mizuseki et al (PNAS 100: 5828-5833, 2003).*
Hoffman et al. (Nat Biotechnol. 23:699-708, 2005).*
Lundqvist et al. (Toxicol in vitro 27: 1565-1569, 2013).*
Schuldiner et al. (PNAS, 97:11307-11312, 2000).*
Dorsky et al (Nature 396 370-373, 1998).*
Extended European Search Report and Office Action corresponding to European Patent Application No. 16802959.3, dated Nov. 16, 2018, 12 pages.
Mains, R.E. et al. "Primary Cultures of Dissociated Sympathetic Neurons" The Journal of Cell Biology, 59:329-345 (1973).
Lumb, Rachael et al. "Sympathoadrenal neural crest cells: The known, unknown and forgotten?" Development Growth & Differentiation, 57:146-157 (2015).
Dupin, Elisabeth et al. "Neural crest progenitors and stem cells: From early development to adulthood" Developmental Biology, 366:83-95 (2012).
Kirino, Kosuke "Efficient derivation of sympathetic neurons from human pluripotent stem cells with a defined condition" Scientific Reports, vol. 8, 11 pages (2018).
Valensi-Kurtz et al. "Enriched Population of PNS Neurons Derived from Human Embryonic Stem Cells as a Platform for Studying Peripheral Neuropathies" PLoS ONE, 5(2):1-10 (2010).
Japanese Office Action corresponding to Japanese Patent Application No. 2017-521742; dated Dec. 27, 2018. 5 pages. Translation.
International Search Report, PCT/JP2016/063006, dated Jun. 28, 2016.
Mizusek K et al. Generation of neural crest-derived peripheral neurons and floor plate cells from mouse and primate embryonic stem cells. PNAS. May 13, 2003; 100(10): 5828-5833.
Hari L et al. Temporal control of neural crest lineage generation by Wnt/β-catenin signaling. Development and Stem Cells. 2012; 139(17): 2107-2117
Fukuta M et al. Derivation of mesenchymal stromal cells from pluripotent stem cells through a neural crest lineage using small molecule compounds with define media. PLOS ONE. Dec. 2, 2014; 9(12) el 12291. 25pp.
Chambers SM et al. Highly efficient neural conversion of human ES and IPS cells by dual inhibition of SMAD signaling. Nature Biotechnology. Mar. 2009; 27(3): 275-280.
Sun Y and Maxwell GD. Ciliary neurotrophic factor (CNTF) has a dose-dependent biphasic effect on the number of adrenergic cells which devop in avian truck neural crest cultures. Neuroscience Letters. 1994; 165: 1-4.

* cited by examiner

*Primary Examiner* — Gregory S Emch
*Assistant Examiner* — Aditi Dutt
(74) *Attorney, Agent, or Firm* — Myers Bigel, P.A.

(57) ABSTRACT

Provided is a method for inducing differentiation of neural crest cells into neurons of the autonomic nervous system, the method including the step of culturing neural crest cells in the presence of at least one of a BMP signaling pathway activator, an SHH signaling pathway inhibitor, and a Wnt signaling pathway inhibitor.

8 Claims, 12 Drawing Sheets

FIG.6
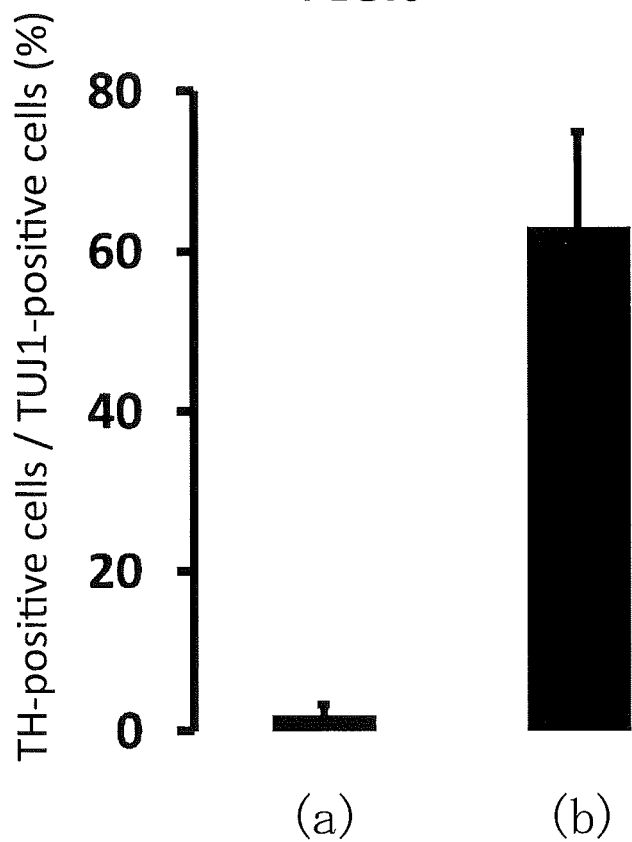
FIG.7A
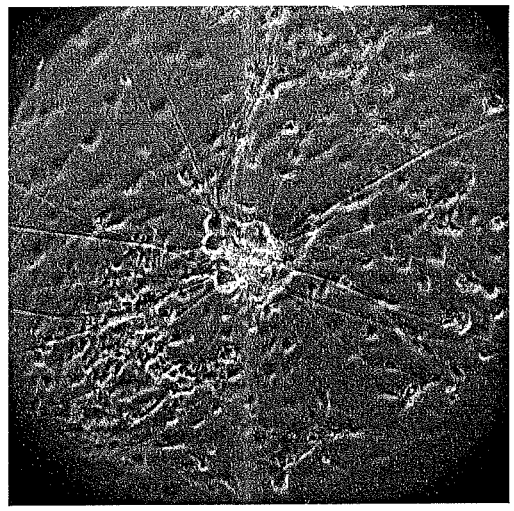
FIG.7B
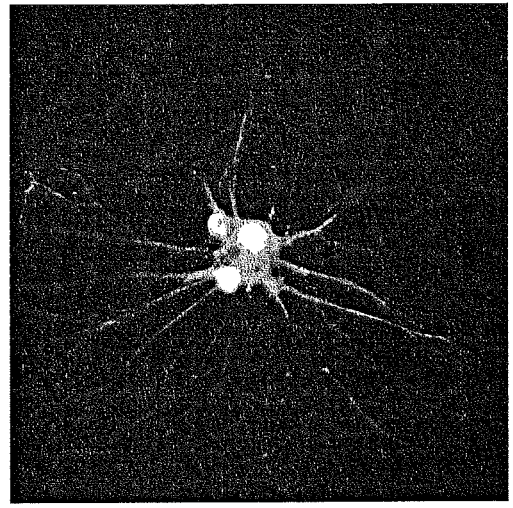
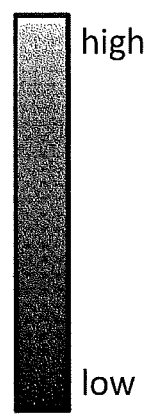

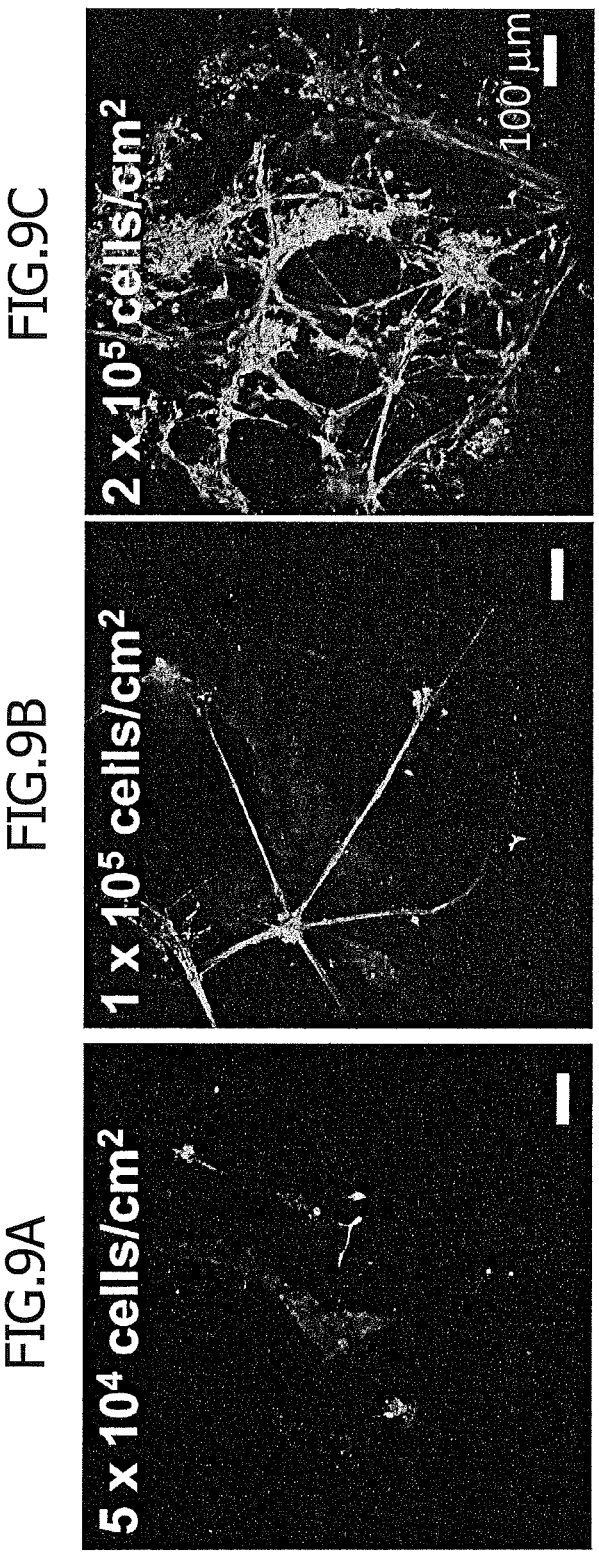

FIG.16
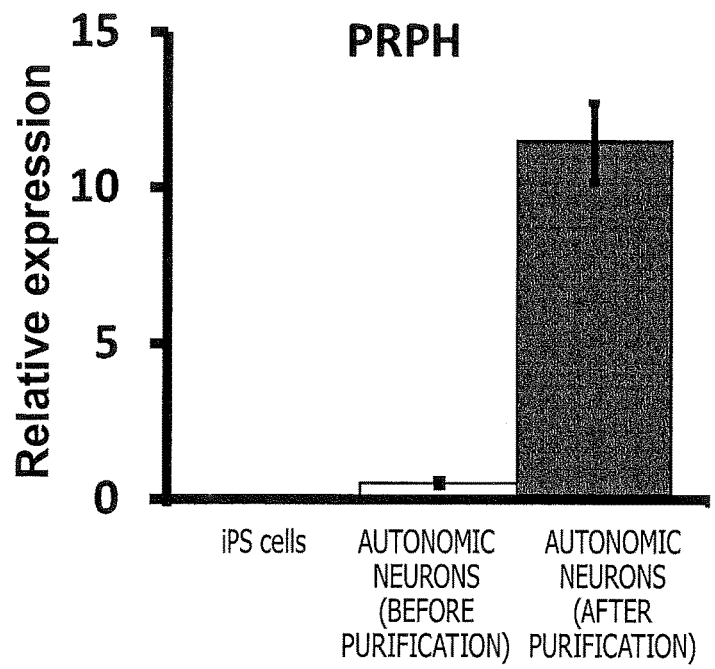
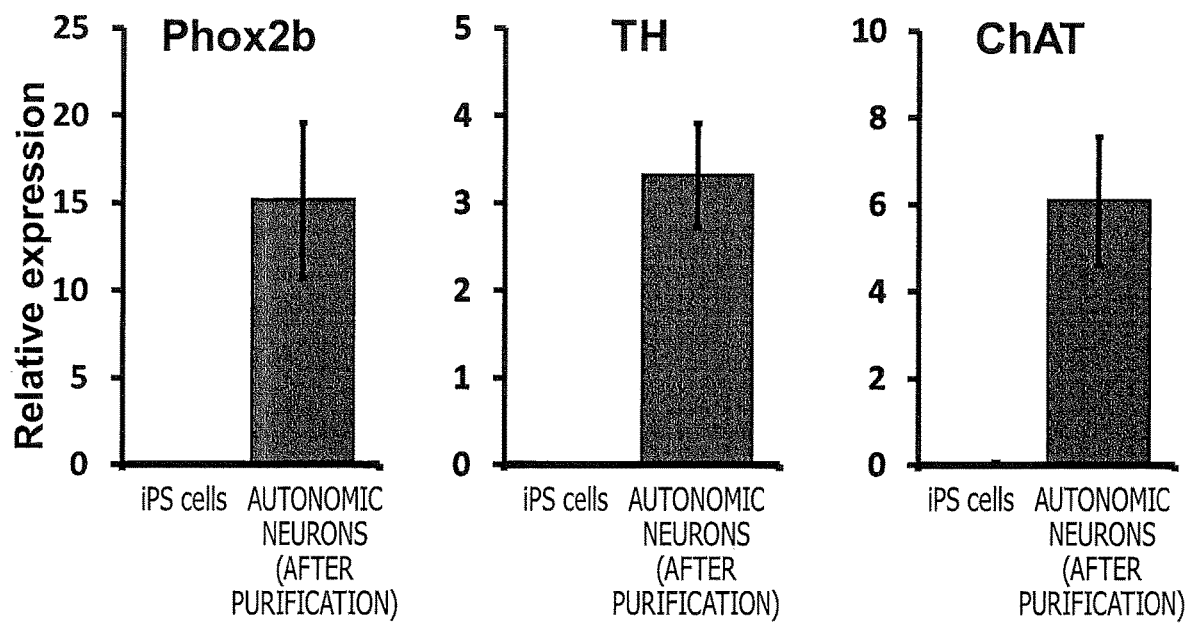

METHOD FOR INDUCING DIFFERENTIATION OF NEURAL CREST CELLS INTO NEURONS OF THE AUTONOMIC NERVOUS SYSTEM

RELATED APPLICATIONS

This application is a 35 U.S.C. § 371 national phase entry of PCT Application PCT/JP2016/063006, filed Apr. 26, 2016, and published in Japanese on Dec. 8, 2016, as International Publication No. WO 2016/194522, and which claims the benefit of Japanese Application No. 2015-112237, filed Jun. 2, 2015, the disclosure of each of which is incorporated herein by reference in its entirety.

TECHNICAL FIELD

The present invention relates to a method for inducing differentiation of neural crest cells into neurons of the autonomic nervous system, neurons of the autonomic nervous system obtained by the differentiation-inducing method, and a kit to be used for the differentiation-inducing method.

BACKGROUND ART

Neurons of the autonomic nervous system are a cell type belonging to the peripheral nervous system and form a neural pathway connecting the central nervous system and each organ. In addition, neurons of the autonomic nervous system have an important role in control of body functions. For example, in psychogenic heartbeat control, stimulation from the center regulates the heart through peripheral autonomic nerves. Furthermore, a deficiency or a functional defect of neurons of the autonomic nervous system leads to malfunction of each organ.

The advent of iPS cells has allowed development support for drugs and cell transplantation therapy using human cells. In these development support for drugs and cell transplantation therapy, it is urgently necessary to create in vitro a peripheral nervous system detecting and regulating stimulation, in addition to a vascular system serving as a supply route to an organ or tissue, so as to provide a material for drug development support such as a material used for compound screening in complex organization including those during organogenesis, as well as compound screening by using a single type of cell.

Although various methods for inducing differentiation of pluripotent stem cells, such as ES cells or iPS cells, into neural crest cells have been studied, there is no technique for selectively inducing neurons of the autonomic nervous system from human pluripotent stem cells. In addition, a technique of inducing selective differentiation of neural crest cells into neurons of the autonomic nervous system does not yet exist.

Mizuseki, et al., Proc Natl Acad Sci USA, 100: 5828-5833 (2003) (hereinafter "Mizuseki 2003") discloses a method for inducing differentiation of mouse or monkey ES cells into neurons of the autonomic nervous system or sensory neurons, comprising inducing neural crest cells with stromal cell-derived inducing activity (SDIA) and BMP4, and further regulating the concentration of the BMP4. Some of the cells induced by the method of Mizuseki 2003 is peripherin-positive and is confirmed as a cell expressing tyrosine hydroxylase. It is thought that the peripherin-positive and tyrosine hydroxylase-positive cells are differentiated into neurons of the autonomic nervous system. However, Mizuseki 2003 discloses that the differentiation induction efficiency by the method into cells being probably of the autonomic nervous system is about 2% to 4%.

Fukuta, et al., PLoS ONE, 9(12): e112291 (2014) (hereinafter "Fukuta 2014") discloses a method for inducing differentiation of human iPS cells and human ES cells into neural crest cells. According to the method described in Fukuta 2014, pluripotent stem cells are induced to differentiate into neural crest cells by being cultured in a CDM medium (Wataya, et al., Proc Natl Acad Sci USA, 105: 11796-11801, 2008) supplemented with a Lefty/Activin/TGF-β pathway inhibitor, SB431542 (SB) or CHIR99021 (CHIR), and cell aggregates are then formed and are induced to differentiate into peripheral nerves with BDNF, GDNF, NT-3, and NGF. Fukuta 2014 discloses the differentiation of pluripotent stem cell-derived neural crest cells into neurons of the peripheral nervous system, but neurons of the autonomic nervous system were not observed, and differentiation induction into neurons of the autonomic nervous system was not intended.

Valensi-Kurtz, et al., PLoS ONE, 5(2): e9290 (2010) (hereinafter "Valensi-Kurtz 2010") discloses the differentiation into neurons of the peripheral nervous system by producing neural progenitor cell aggregates from ES cells with a culture medium supplemented with FGF2 and noggin, and then culturing the cells on a cover-slip coated with laminin. Valensi-Kurtz 2010 aims to induce differentiation of pluripotent stem cells into a peripheral nervous system, and reports that 70% or more of the cells differentiated into a peripheral nervous system and 30% of the cells therein differentiated into sensory neurons. Also, in the method for induction of Valensi-Kurtz 2010, cells expressing peripherin and tyrosine hydroxylase are observed, but the rate of such cells was merely 3% to 5% of the peripherin-positive cells.

Thus, several methods of inducing differentiation of pluripotent stem cells or neural crest cells into a peripheral nervous system have been reported; however, a method for specifically inducing to an autonomic nervous system among peripheral nerves has not yet been reported. For example, in Mizuseki 2003 and Valensi-Kurtz 2010, as noted above, differentiation induction of pluripotent stem cells into neurons of the peripheral nervous system has been attempted, but it was merely reported that the sample after differentiation induction contains tyrosine hydroxylase (TH)-positive neurons at low level (it was reported that at most, about 5% of the cells showed a TH-positive reaction), and cells of a variety of peripheral nervous systems are mixed. TH is a marker protein for the autonomic nervous system, and it is perceived that even the methods of Mizuseki 2003 and Valensi-Kurtz 2010 induce some cells into the autonomic nervous system; however, the methods do not stand practical use for application to therapy because of the low differentiation efficiency. In addition, the methods disclosed in Mizuseki 2003, Fukuta 2014, and Valensi-Kurtz 2010 need to be cultured for long periods of time to induce differentiation to the peripheral nervous system, and a method for inducing differentiation within a shorter period of time is therefore demanded.

CITATION LIST

Mizuseki, et al., Proc Natl Acad Sci USA, 100: 5828-5833 (2003)
Fukuta, et al., PLoS ONE, 9(12): e112291 (2014)
Valensi-Kurtz, et al., PLoS ONE, 5(2): e9290 (2010)

SUMMARY OF INVENTION

Technical Problem

The present invention was made in view of the above-described problems, and provides a method for inducing differentiation of neural crest cells into neurons of the autonomic nervous system within a short period of time and with a high efficiency.

Solution to Problem

In order to solve the above-described problems, the present inventors have diligently researched and have found that neural crest cells can be induced to specifically differentiate into neurons of the autonomic nervous system within a shorter period of time and with a high efficiency by activating the BMP signaling pathway of the neural crest cells during the culture and by inhibiting the sonic hedgehog signaling pathway and the Wnt signaling pathway, before a step of inducing differentiation of neural crest cells into neurons (for example, in the method of Fukuta 2014, the differentiation induction treatment step using BDNF, GDNF, NT-3, and NGF). The present invention has been accomplished based on the findings described above.

That is, the present invention relates to:

[1] A differentiation-inducing method for producing neurons of the autonomic nervous system from neural crest cells, the method comprising the step of:

(a) culturing the neural crest cells in the presence of at least one agent selected from the group consisting of BMP signaling pathway activators, SlHH signaling pathway inhibitors, and Wnt signaling pathway inhibitors.

An embodiment of the differentiation-inducing method of the present invention for producing neurons of the autonomic nervous system from neural crest cells relates to:

[2] The differentiation-inducing method according to the embodiment [1], comprising the step of:

(b) after the step (a), culturing the neural crest cells in the presence of at least one compound selected from the group consisting of cAMP production promoters, BDNF signaling pathway activators, CNTF signaling pathway activators, GDNF signaling pathway activators, NGF signaling pathway activators, NT-3 signaling pathway activators, and ascorbic acid.

Another embodiment of the differentiation-inducing method of the present invention for producing neurons of the autonomic nervous system from neural crest cells relates to:

[3] The differentiation-inducing method according to the embodiment [1] or [2], wherein the step (a) is a step of culturing the neural crest cells in the presence of a combination of a BMP signaling pathway activator, an SHH signaling pathway inhibitor, and a Wnt signaling pathway inhibitor.

Another embodiment of the differentiation-inducing method of the present invention for producing neurons of the autonomic nervous system from neural crest cells relates to:

[4] The differentiation-inducing method according to any of the embodiments [1] to [3], wherein the neural crest cells are derived from an organism.

Another embodiment of the differentiation-inducing method of the present invention for producing neurons of the autonomic nervous system from neural crest cells relates to:

[5] The differentiation-inducing method according to any of the embodiments [1] to [3], wherein the neural crest cells are derived from pluripotent stem cells.

Another embodiment of the differentiation-inducing method of the present invention for producing neurons of the autonomic nervous system from neural crest cells relates to:

[6] The differentiation-inducing method according to the embodiment [5], comprising the step of:

before the step (a), culturing the pluripotent stem cells in the presence of a combination of compounds selected from the group consisting of BMP signaling pathway inhibitors, TGF signaling pathway inhibitors, Wnt signaling pathway activators, FGF signaling pathway activators, and EGF signaling pathway activators so as to induce the pluripotent stem cell-derived neural crest cells.

Another embodiment of the differentiation-inducing method of the present invention for producing neurons of the autonomic nervous system from neural crest cells relates to:

[7] The differentiation-inducing method according to embodiment [5] or [6], the method further comprising the step of:

preculturing the pluripotent stem cells with a culture medium supplemented with Y-27632.

Another embodiment of the differentiation-inducing method of the present invention for producing neurons of the autonomic nervous system from neural crest cells relates to:

[8] The differentiation-inducing method according to any one of the embodiments [1] to [7], wherein in the step (a), the BMP signaling pathway activator is at least one BMP signaling pathway activator selected from the group consisting of BMP2, BMP4, BMP7, and BMP2/4; or the SHH signaling pathway inhibitor is at least one SHH signaling pathway inhibitor selected from the group consisting of SANT, JK184, and Jervine; or the Wnt signaling pathway inhibitor is at least one Wnt signaling pathway inhibitor selected from the group consisting of IWR, XAV939, and IWP.

Another embodiment of the differentiation-inducing method of the present invention for producing neurons of the autonomic nervous system from neural crest cells relates to:

[9] The differentiation-inducing method according to any one of the embodiments [2] to [8], wherein the neural crest cells in the step (b) are seeded at a concentration of $2 \times 10^5$ cells/cm$^2$ or more.

Another embodiment of the differentiation-inducing method of the present invention for producing neurons of the autonomic nervous system from neural crest cells relates to:

[10] The differentiation-inducing method according to any one of the embodiments [2] to [8], wherein the step (b) is a step of culturing the cells in the presence of a BDNF signaling pathway activator and a CNTF signaling pathway activator, wherein the BDNF signaling pathway activator is 10 to 100 ng/ml of BDNF, and the CNTF signaling pathway activator is 10 to 100 ng/ml of CNTF.

Another aspect of the present invention relates to:

[11] Neurons of the autonomic nervous system prepared by the method according to any one of the embodiments [1] to [10].

Another aspect of the present invention relates to:

[12] A kit for differentiating neural crest cells into neurons of the autonomic nervous system, the kit comprising at least one agent selected from the group consisting of BMP signaling pathway activators, SHH signaling pathway inhibitors, and Wnt signaling pathway inhibitors.

Advantageous Effects of Invention

According to the differentiation-inducing method of the present invention, neural crest cells can be induced to selectively differentiate into neurons of the autonomic nervous system at a high rate. The differentiation-inducing method of the present invention can induce differentiation into neurons of the autonomic nervous system by culture within a shorter period of time compared to known differentiation-inducing methods.

Furthermore, according to the differentiation-inducing method of the present invention, neural crest cells can be induced to selectively differentiate into sympathetic neurons or parasympathetic neurons constituting autonomic nervous system.

The neurons of the autonomic nervous system obtained by the present invention can be used for therapeutic application by transplantation as an approach to regenerative medicine or can be used for a test for investigating the mechanism of differentiation of neural crest cells into neurons of the autonomic nervous system or for establishing a therapeutic method for a disease associated with peripheral nerves.

BRIEF DESCRIPTION OF DRAWINGS

FIG. 2 shows images, taken under a fluorescence microscope, of immunostained neurons of the autonomic nervous system differentiated from iPS cells by the method described in "2. Differentiation induction into autonomic nervous system" in the following Example.

FIG. 3 shows images, taken under a fluorescence microscope, of immunostained neurons of the autonomic nervous system differentiated from iPS cells by the method described in "2. Differentiation induction into autonomic nervous system" in the following Example.

FIG. 6 is a graph showing differentiation induction efficiencies into neurons of the autonomic nervous system in a known method for inducing differentiation of pluripotent stem cell-derived neural crest cells into neurons of the peripheral nervous system (FIG. 5(a)) and in the method described in "2. Differentiation induction into autonomic nervous system" in the following Example (FIG. 5(b)). In the graph, (a) shows the differentiation induction efficiency in the known differentiation-inducing method; (b) shows the differentiation induction efficiency in the method described in "2. Differentiation induction into autonomic nervous system" in the following Example; and the vertical axis shows the rate of the number of TH-positive cells to the number of TUJ1-positive nerve cells.

FIG. 7 shows a phase contrast image (FIG. 7(a)) of cells induced by the method described in "2. Differentiation induction into autonomic nervous system" in the following Example (cells obtained by culture for 35 days in differentiation-inducing step 6) and an image (FIG. 7(b)) of the cells obtained by imaging intracellular calcium with fluorescent indicator.

FIG. 8 shows the results of observation over time of calcium influx with fluorescent indicator when electric stimulation was applied multiple times to the cells induced by the method described in "2. Differentiation induction into autonomic nervous system" (differentiation-inducing step 6) in the following Example.

FIG. 9 shows images, taken under a fluorescence microscope, of cells subjected to differentiation induction in the differentiation-inducing step 6 in the following Example at a cell-seeding concentration of (a) $5\times10^4$ cells/cm$^2$, (b) $1\times10^5$ cells/cm$^2$, or (c) $2\times10^5$ cells/cm$^2$ and immunostained with an anti-TH antibody.

FIG. 16 includes graphs showing increases in the expression level of peripheral neuron marker (peripherin), autonomic nervous system marker (Phox2b), sympathetic neuron marker (TH), and parasympathetic neuron marker (ChAT) in the cells after drug selection culture.

DESCRIPTION OF EMBODIMENTS

Figure 1:
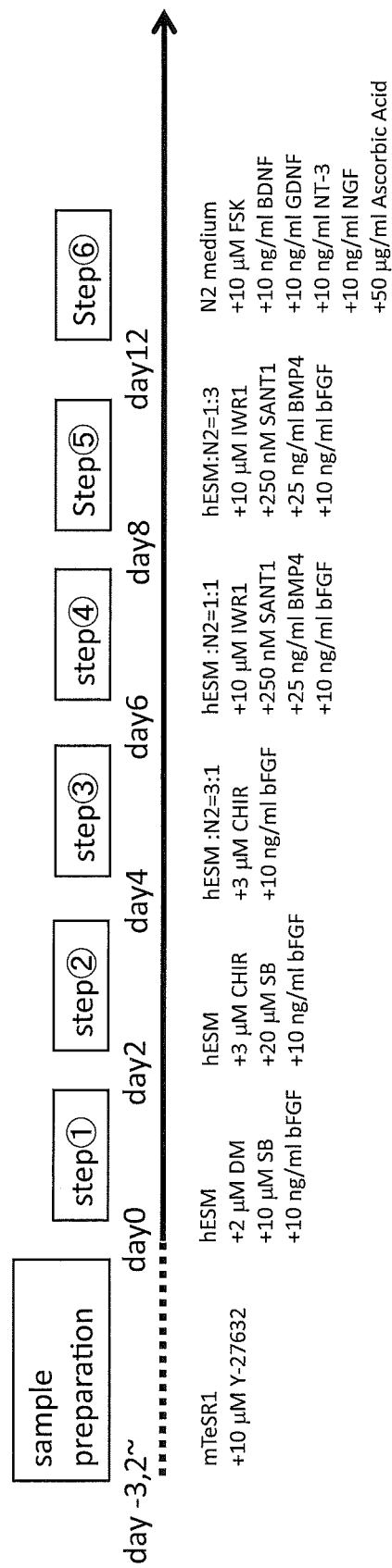
FIG. 1 is a diagram showing a method for inducing differentiation of pluripotent stem cells into neurons of the autonomic nervous system in an embodiment of the present invention. This method includes a preculturing step of pluripotent stem cells and six cell-culturing steps, and the composition of the culture medium and the number of culture days in each of the culturing steps is disclosed.

The nerves of vertebrates are roughly classified into central nervous system and peripheral nervous system. The peripheral nervous system are classified into somatic nervous system, which are motor and sensory neurons, and autonomic nervous system, which are sympathetic and parasympathetic neurons. The differentiation-inducing method of the present invention is a method for differentiating neural crest cells into neurons of the autonomic nervous system in the peripheral nervous system.

The present inventors found that neurons of the autonomic nervous system can be induced by preliminary culture for activating the BMP signaling pathway or inhibiting the sonic hedgehog signaling pathway or the Wnt signaling pathway in the step of differentiation induction culture of neural crest cells.

That is, neural crest cells, which originally have an ability to differentiate into neurons of the peripheral nervous system and the like other than neurons of the autonomic nervous system, can be determined to differentiate into neurons of the autonomic nervous system by culturing the cells under conditions that can activate or inhibit the above-mentioned signaling pathways before the differentiation induction culture into neurons of the peripheral nervous system or as a first half step of the differentiation induction culture.

Herein, throughout the present specification, the term "neural crest cells" refers to cell population that is delaminated from a neural crest, a structure that is temporarily formed between surface ectoderm and neural plate in the early development of a vertebrate, and is induced into various sites in an embryo after epithelial-mesenchymal transition. Neural crest cells are known to differentiate into various cell types, such as neurons belonging to various peripheral nervous system, Schwann cells, melanocytes, and cardiac smooth muscle cells.

The term "neural crest cells" in the present specification includes neural crest cells differentiated from pluripotent stem cells by differentiation induction treatment, neural crest cells collected from an organism, and subcultured cells thereof.

The neural crest cells used in the differentiation-inducing method of the present invention may be not only neural crest cells obtained by differentiation of pluripotent stem cells as described above, but also organism-derived neural crest cells collected from an organism, subcultured cells thereof, cryopreserved neural crest cells, and the like. When neural crest cells are collected from an organism, the neural crest cells can be collected from a neural crest of a fetus or an adult or another tissue (such as bone marrow, heart, cornea, iris, dental pulp, and olfactory mucosa). The collected neural crest cells can be subcultured with a medium supplemented with, for example, epidermal growth factor (EGF) and basic fibroblast growth factor (bFGF) (Fukuta 2014).

The neural crest cell and the pluripotent stem cell used in the present invention are preferably mammalian-derived cells. Examples of the mammalian include mice, rats, guinea pigs, hamsters, rabbits, cats, dogs, sheep, pigs, cows, horses, goats, monkeys, and humans.

Throughout the present specification, the term "pluripotent stem cell" refers to an undifferentiated cell having "self-renewal potential" capable of proliferating while maintaining its undifferentiated state and "differentiation pluripotency" capable of differentiating into any of three germ layers. Examples of the pluripotent stem cell include, but not limited to, induced pluripotent stem cells (iPS cells), embryonic stem cells (ES cells), Muse cells, which are isolated from bone marrow mesenchymal cells, embryonic germ cells (EG cells), which are derived from primordial germ cells, and multipotent germ-stem cells (mGS cells), which are isolated during the culture step for establishing GS cells from testicular tissue. The ES cells may be generated by nuclear reprogramming of somatic cells. The above-mentioned pluripotent stem cells can each be obtained by known methods.

Herein, the induced pluripotent stem cell (iPS cell) is a differentiated somatic cell transfected with a small number of genes and capable of being reprogrammed into various tissue or organ cells. In the present invention, the iPS cells used for inducing neural crest cells may be derived from primary culture cells of somatic cells collected from an appropriate donor or an established cell line. Examples of the established cell line include a human established cell line MRC-5 cells. Since iPS cells can be induced to differentiate into any germ layer cells, the somatic cells used for preparation of the iPS cells may be essentially derived from any cells of germ layer of ectodermal and endodermal. Cells that are low in invasiveness and easy to collect, such as cells of skin, hair, gingiva, and blood, are suitable as somatic cells used for preparation of iPS cells of this aspect. The iPS cells can be prepared in accordance with a method known in the art. Specifically, for example, a preparation method described in "*Hito Tanousei Kan-saibo no Iji-Baiyo Purotokoru* (Maintenance culture protocol of human pluripotent stem cells) Second Edition, 2010 (RIKEN Center for Developmental Biology).

In the present invention, the ES cells used for inducing neural crest cells can be established by collecting an inner cell mass from the blastocyst of a fertilized egg of a target animal by a known method and culturing the inner cell mass on feeder cells derived from fibroblasts. Alternatively, ES cells established by culturing early embryos produced by nuclear transplantation of somatic cell nuclei can also be used. The term "ES cells" in the present specification includes ES cells obtained by modifying the genes of the above-mentioned ES cells by a genetic engineering technique.

(1. Regulation of Intracellular Signals of Neural Crest Cells Before Differentiation Induction)

As described above, the present invention relates to a method of preliminarily performing culture for activating the BMP signaling pathway or inhibiting the sonic hedgehog signaling pathway or the Wnt signaling pathway in the step of differentiation induction culture of neural crest cells. Hereinafter, in the present specification, the culture being preliminarily performed is referred to as "regulation culture of neural crest cells".

Herein, the BMP signaling pathway means an intracellular signal transduction mechanism specific to bone morphogenetic protein (BMP). The intracellular signal of BMP is known to be transmitted through a transmembrane serine-threonine kinase receptor, which is classified into type I and type II. The type II receptor bound to BMP phosphorylates a region called a GS domain, which is present in an intracellular region of the type I receptor and is rich in serine and glycine residues, so as to activate the kinase of the type I receptor. The activated type I receptor phosphorylates two serine residues of an SVS motif, which is composed of serine-valine-serine residues and is present at the C-terminals of Smad1, Smad5, and Smad8 each called receptor-regulated Smad protein (R-Smad) present in cytoplasm, so as to activate the group of these transcription regulators. The activated BMP receptor is also known to activate, for example, p38 mitogen-activated protein kinase (p38 MAPK). Two molecules of phosphorylated R-Smad and one molecule of Smad4 present in cytoplasm form a heterotrimeric complex, which is transferred to the nucleus and recognizes and binds to a specific nucleotide sequence rich in GC sequences on the DNA to regulate the transcription of the target gene.

The BMP signaling pathway activator used in the present invention is, for example, a compound that can activate the BMP signaling pathway described above. Examples thereof include BMP receptor agonists, BMP family proteins, and artificially synthesized chimeric proteins, specifically, BMP2, BMP4, BMP7, and BMP2/4; and preferred is BMP4. The BMP signaling pathway activator used in the present invention may be any material that can activate the BMP signaling pathway, and known materials can be used without being limited to the above-mentioned compounds. As the BMP signaling pathway activator, a single compound may be used, or a combination of a plurality of compounds may be used.

The concentration of a reagent that is added to a culture medium for activating the BMP signaling pathway can be appropriately set by a skilled person in the art to a range that activates the BMP signaling pathway to facilitate the differentiation induction of neural crest cells into autonomic nervous system lineages. For example, in the case of using BMP4 as a BMP signaling pathway activator, the concentration is preferably within a range of 0.1 to 100 ng/ml, and more preferably, within a range of 5 to 50 ng/ml.

The SHH signaling pathway is a signaling pathway that is mainly regulated by a ligand sonic hedgehog. The sonic hedgehog is translated as a precursor of about 45 kDa and is then auto-catalytically cleaved into an N-terminal signal domain (SHH-N) of 20 kDa and a C-terminal (SHH-C) of 25 kDa. On this cleavage, a cholesterol molecule is added to the C-terminal of SHH-N, leading to release to the outside of the cell or interaction with a receptor. SHH is known to bind to its receptor PTCH1 (Patched-1). In an SHH-free condition, PTCH1 inhibits SMO (Smoothened) and suppresses its downstream pathway. It is thought that the presence of SHH eliminates the inhibition of SMO to activate the glioma-associated oncogene (GLI) transcription factor and that the activated GLI accumulates in the nucleus to regulate transcription of the target gene of hedgehog.

The SI signaling pathway inhibitor used in the present invention is, for example, a compound that can inhibit the SHH signaling pathway described above. Examples thereof include SMO receptor antagonists and GLI transcription factor inhibitors, specifically, SANT, JK184, and jervine; and preferred is SANT. The SHH signaling pathway inhibitor used in the present invention may be any material that can inhibit the SHH signaling pathway, and known materials can be used without being limited to the above-mentioned compounds. As the SHH signaling pathway inhibitor, a single compound may be used, or a combination of a plurality of compounds may be used.

The concentration of a reagent that is added to a culture medium for inhibiting the SHH signaling pathway can be appropriately set by a person skilled in the art to a range that inhibits the SHH signaling pathway to facilitate the differentiation induction of neural crest cells into autonomic nervous system lineages. For example, in the case of using SANT as the SHH signaling pathway inhibitor, the concentration is preferably within a range of 20 nM to 2 µM and more preferably within a range of 100 to 500 nM.

The Wnt signaling pathway is an intracellular signal transduction mechanism activated by the action of Wnt on a cell. A large number of Wnt genes exist on the genome of humans or mice. As Wnt receptors, ten types of seven-pass transmembrane receptors Frizzled are known. As co-receptors of the Wnt receptor, one-pass transmembrane receptors, such as LRP5, LRP6, Ror1, Ror2, and Ryk, are known. There are at least three types of this signaling pathway: (i) β-catenin pathway that regulates gene expression through β-catenin, (ii) planar cell polarity (PCP) pathway that regulates the planar polarity of a cell, and (iii) $Ca^{2+}$ pathway that facilitates intracellular mobilization of $Ca^{2+}$.

In the present invention, inhibition of the Wnt signaling pathway is aimed at inhibition of, in particular, the above-mentioned (i) β-catenin pathway that regulates gene expression through β-catenin. Neural crest cells can be induced to differentiate into neurons of the autonomic nervous system by inhibiting the Wnt signaling pathway, in particular, the pathway (i). As a preferred embodiment, for example, Wnt-3a, which is one of the Wnt family, may be inhibited. Wnt-3a binds together with LRP5/6 transmembrane protein to a Frizzled receptor protein to increase the intracellular β-catenin concentration through an intracellular cascade. It is known that a Wnt/β-catenin responsive gene is finally activated.

In the present invention, inhibition of the Wnt signaling pathway is not limited to such inhibition of the signaling pathway depending on Wnt-3a (e.g., binding to Wnt-3a itself or inhibition of binding to its receptor) and includes inhibition of Wnt-1 or another Wnt-related signaling pathway or inhibition of a downstream signaling pathway thereof.

The Wnt signaling pathway inhibitor used in the present invention is, for example, a compound that can inhibit the Wnt signaling pathway, such as a compound that binds to the Wnt ligand (e.g., Wnt-3a) itself, a Wnt ligand receptor antagonist, and a compound that inhibits a signaling pathway downstream the Wnt ligand. Examples thereof include IWR, XAV939, and IWP; and preferred is IWR. The Wnt signaling pathway inhibitor used in the present invention is not limited to an inhibitor that inhibits the Wnt signaling pathway and may be an inhibitor that can inhibit a Wnt-independent β-catenin signal. The Wnt signaling pathway inhibitor used in the present invention may be any material that can inhibit the Wnt signaling pathway or Wnt-independent β-catenin signal, and known materials can be used without being limited to the above-mentioned compounds. As the Wnt signaling pathway inhibitor, a single compound may be used, or a combination of a plurality of compounds may be used.

The concentration of a reagent that is added to a culture medium for inhibiting the Wnt signaling pathway can be appropriately set by a person skilled in the art to a range that inhibits the Wnt signaling pathway to facilitate the differentiation induction of neural crest cells into autonomic nervous system lineages. For example, in the case of using IWR as the Wnt signaling pathway inhibitor, the concentration is preferably within a range of 0.5 to 100 µM and more preferably within a range of 2 to 20 µM.

The regulation culture of neural crest cells of the present invention may involve performing, as long as the neural crest cells can be induced to differentiate into neurons of the autonomic nervous system, at least one of
(1) activation of a BMP signaling pathway,
(2) inhibition of a sonic hedgehog signaling pathway, and
(3) inhibition of a Wnt signaling pathway.
A method of activating or inhibiting the pathways by performing two of (1) to (3) is preferable, and a method of activating or inhibiting the pathways by performing all three of (1) to (3) is most preferable.

When the pathways are activated or inhibited by performing two or more of (1) to (3), the activation or inhibition of each pathway may be performed at the same time, may be performed at different timings, or may be performed by combination thereof, as long as neural crest cells can be induced to differentiate into neurons of the autonomic nervous system.

When pluripotent stem cells are induced to differentiate into neural crest cells and the neural crest cells are then further induced to differentiate into neurons of the autonomic nervous system, the method of activating or inhibiting the pathways according to (1) to (3) may be incorporated in a last half of the culture step of inducing differentiation of pluripotent stem cells into neural crest cells.

The BMP signaling pathway activator, the SHH signaling pathway inhibitor, and the Wnt signaling pathway inhibitor can be used by adding to a base medium, such as hESM, N-2 medium, or a mixture thereof. A preferred base medium is a medium mixture of hESM and N-2 medium. When the medium mixture is used, the ratio of hESM and N-2 medium is preferably within a range of 1:3 to 3:1. The base medium may be other known medium that can induce differentiation of neural crest cells into neurons of the autonomic nervous system.

The base medium may contain, for example, bFGF and EGF as components other than the BMP signaling pathway activator, the SHH signaling pathway inhibitor, and the Wnt signaling pathway inhibitor. From the viewpoint of cell proliferation and neuronal differentiation, bFGF is preferably contained as a component other than the BMP signaling pathway activator, the SHIH signaling pathway inhibitor, and the Wnt signaling pathway inhibitor.

The step of culturing neural crest cells in a medium supplemented with at least one agent selected from the group consisting of BMP signaling pathway activators, SHH signaling pathway inhibitors, and Wnt signaling pathway inhibitors is preferably performed for 5 to 7 days and more preferably for 6 days.

The regulation culture of neural crest cells of the present invention may be performed by an adherent culture method or may be performed by a floating culture method.

As an embodiment, the process of activating or inhibiting the signaling pathways according to (1) to (3) may be composed of two or more steps. As a preferred embodiment composed of a plurality of steps, for example, a culture step using a medium mixture of hESM and N-2 medium at a ratio of 1:1 (v/v) as the base medium is performed for 2 to 3 days, preferably for 2 days, and a culture step using a medium mixture of hESM and N-2 medium at a ratio of 1:3 (v/v) as the base medium is then performed for 3 to 5 days, preferably for 4 days. Thus, it is preferred to increase the concentration of N-2 medium relative to that of hESM in a last half of the culture. Such combination of two or more culture steps with different compositions of the base media can facilitate neuronal differentiation and is preferred. Such combination of two or more culture steps can regulate the differentiation induction of cells overtime and can synchronize the differentiation stage of the cells during the culture. Such synchronization of the differentiation stage of the cells during the differentiation induction allows the subsequent differentiation induction to be readily regulated (in other words, an appropriate compound can be utilized at an appropriate timing to easily obtain an expected effect), leading to an increase in the differentiation induction efficiency.

A preferred embodiment of the culture step of performing at least one of (1) the activation of the BMP signaling pathway, (2) the inhibition of the sonic hedgehog signaling pathway, and (3) the inhibition of the Wnt signaling pathway will now be specifically disclosed (the following example is a method for activating or inhibiting the pathways by performing three of (1) to (3)).

The method includes:
a first culture step of performing culture with a medium mixture of hESM and N-2 medium (1:1 (v/v)) containing 10 µM IWR-1, 250 nM SANT1, 25 ng/ml BMP4, and 10 ng/ml bFGF for 2 to 3 days, preferably for about 2 days; and
a second culture step of performing culture with a medium mixture of hESM and N-2 medium (1:3 (v/v)) containing 10 µM IWR-1, 250 nM SANT1, 25 ng/ml BMP4, and 10 ng/mi bFGF for 3 to 5 days, preferably for about 4 days.

In the culture for 2 or more days, the entire culture medium is preferably replaced with a fresh medium every 2 days. The step of activating or inhibiting the signaling pathways (1) to (3) is not limited to the above-mentioned example, and the composition of each culture medium, the culture period with each medium, and the number of culture steps can be appropriately designed as long as neural crest cells can be induced to differentiate into neurons of the autonomic nervous system.

(2-1. Method for Inducing Differentiation of Neural Crest Cells into Neurons of the Autonomic Nervous System)

In the method of the present invention, after the regulation culture of neural crest cells, differentiation induction treatment is performed.

The differentiation induction treatment can be performed by a known method (e.g., the method described in Mizuseki 2003 or Fukuta 2014). For example, culture can be performed using, for example, a DMEM/Ham's F-12 medium (Wako: 048-29785), human stem cell medium (hESM), or N-2 medium as the base medium in the presence of a compound or a plurality of compounds selected from the group of cAMP production promoters, BDNF signaling pathway activators, CNTF signaling pathway activators, GDNF signaling pathway activators, NGF signaling pathway activators, NT-3 signaling pathway activators, ascorbic acid, and the like. Such compounds may be a known compound that activates of the target signaling pathway or facilitates the generation of cAMP. Specifically, although the examples are not limited to the following compounds, for example, Forskolin (FSK), L-858051, and a cAMP analog DB-cAMP can be used as the cAMP production promoter; brain-derived neurotrophic factor (BDNF) can be used as the BDNF signaling pathway activators; ciliary neurotrophic factor (CNTF) can be used as the CNTF signaling pathway activator, glial cell-derived neurotrophil factor (GDNF) can be used as the GDNF signaling pathway activator, nerve growth factor-β (NGF) can be used as the NGF signaling pathway activators; and neurotrophin-3 (NT-3) can be used as the NT-3 signaling pathway activator. Furthermore, the base medium can be appropriately supplemented with, for example, knockout serum replacement (KSR), MEM non-essential amino acids solution (NEAA), monothioglycerol solution, penicillin-streptomycin solution (P/S), or an N2 supplement.

The concentration of FSK contained in a culture medium is preferably within a range of 5 to 50 µM. The concentration of BDNF contained in a culture medium is preferably within a range of 1 to 100 ng/ml. The concentration of CNTF contained in a culture medium is preferably within a range of 1 to 100 ng/ml. The concentration of GDNF contained in a culture medium is preferably within a range of 1 to 50 ng/ml. The concentration of NT-3 contained in a culture medium is preferably within a range of 1 to 50 ng/ml. The concentration of NGF contained in a culture medium is preferably within a range of 1 to 50 ng/ml. The concentration of ascorbic acid contained in a culture medium is preferably within a range of 10 to 100 µg/ml. The selection of differentiation-inducing reagents and determination of the concentrations thereof can be appropriately performed depending on, for example, conditions of the reagents used in combination, without being limited to the examples above.

The culture of inducing differentiation of neural crest cells into neurons of the autonomic nervous system is performed by an adherent culture method. The plate used for the culture is preferably coated with PLO, laminin, fibronectin, poly-D-lysine, Matrigel, or a combination thereof and is more preferably coated with both PLO and laminin.

In an embodiment of the differentiation induction treatment, neural crest cells can be induced to differentiate into neurons of the autonomic nervous system by culturing the neural crest cells on a plate coated with PLO and laminin, using N-2 medium supplemented with the following reagents, in which 10 μM FSK, 10 ng/ml BDNF, 10 ng/ml GDNF, 10 ng/ml NT-3, 10 ng/ml NGF, and 50 μg/ml ascorbic acid are contained. In the culture under the above-mentioned conditions, the culture period is preferably 10 to 30 days and more preferably 20 days.

Thus, the activation or inhibition of the pathways according to (1) to (3) before the culture for differentiation induction of neural crest cells into neurons of the autonomic nervous system can increase the efficiency of inducing differentiation into the autonomic nervous system and further can decrease the culture time necessary for differentiation induction.

For example, in the differentiation-inducing method described in Valensi-Kurtz 2010 (a method for inducing differentiation of pluripotent stem cell-derived neural crest cells into peripheral nervous system cells), at least 60 days are necessary as the culture period. However, in the differentiation-inducing method of the present invention, differentiation can be induced within a culture period of 40 days or less and preferably 30 days or less.

Differentiation induction of neural crest cells into autonomic nervous system cells by the differentiation induction culture can be confirmed by, for example, an immunostaining method as shown in the following Example. More specifically, differentiation induction can be confirmed by immunostaining a protein such as TUJ1 serving as a differentiation marker for neurons, peripherin serving as a marker protein for peripheral neurons, tyrosine hydroxylase (TH) serving as a marker protein for sympathetic neurons, or choline acetyltransferase (ChAT) serving as a marker protein for parasympathetic neurons. The cells obtained after differentiation induction culture by the present invention express the above-mentioned three marker proteins and can be confirmed to be neurons of the autonomic nervous system.

The method for immunostaining can be performed under the conditions described in the following example or can be appropriately implemented in accordance with a known method by a person skilled in the art.

According to the differentiation-inducing method of the present invention for producing neurons of the autonomic nervous system from neural crest cells, the efficiency of inducing differentiation of neural crest cells into neurons of the autonomic nervous system can be 40% or more and is more preferably 50% or more and most preferably 70% or more.

In the present specification, the efficiency of inducing neural crest cells into neurons of the autonomic nervous system means the ratio of the number of TH-positive cells to the number of TUJ1-positive neurons. The number of TUJ1-positive or TH-positive neurons can be determined by labeling the cells with fluorescence by, for example, immunostaining and counting the cells using an image taken with, for example, a cooled CCD camera.

The neurons of the autonomic nervous system obtained by the differentiation-inducing method of the present invention for producing neurons of the autonomic nervous system from neural crest cells can be in a state matured into functional neurons. Whether the neurons obtained by differentiation induction are functional or not can be evaluated by, for example, as shown in Example 5 below, investigating the response against electric stimulation by calcium imaging. As an example, a fluorescent calcium indicator, such as fluo-4/AM, is loaded in cells, and influx of calcium is observed by applying electric stimulation to the cells. Alternatively, the function of the differentiation induced cells may be evaluated by any known method.

In the neurons of the autonomic nervous system obtained by the differentiation-inducing method of the present invention for producing neurons of the autonomic nervous system from neural crest cells, occurrence of calcium signals having waveform and duration specific to neurons can be observed. That is, neurons of the autonomic nervous system obtained by the differentiation-inducing method of the present invention can be obtained as functionally mature neurons.

(2-2. Method for Inducing Differentiation of Neural Crest Cells into Sympathetic Neurons)

As an embodiment, in the differentiation induction culture in the section 2-1., when neural crest cells are seeded at a concentration of $2 \times 10^5$ cells/cm$^2$ or more, the neural crest cells can be induced to selectively differentiate into neurons of the autonomic nervous system, in particular, into sympathetic neurons. The concentration of seeded neural crest cells is preferably within a range of $2 \times 10^5$ to $5 \times 10^5$ cells/cm$^2$ and more preferably within a range of $4 \times 10^5$ to $5 \times 10^5$ cells/cm$^2$. The culture conditions other than the seeding concentration of neural crest cells may be the same as those of the differentiation induction culture in the section 2-1.

According to this embodiment, the efficiency of inducing differentiation of neural crest cells into sympathetic neurons can be 30% or more. In the present specification, the efficiency of inducing differentiation of neural crest cells into sympathetic neurons mean the ratio of the number of TH-positive cells to the total cell number in the dish. The TH-positive cells can be identified by, for example, immunostaining and can be counted.

(2-3. Method for Inducing Differentiation of Neural Crest Cells into Parasympathetic Neurons)

As an embodiment, in the differentiation induction culture in the section 2-1., when a culture medium supplemented with 10 to 100 ng/ml BDNF and 10 to 100 ng/ml CNTF is used, neural crest cells can be induced to selectively differentiate into neurons of the autonomic nervous system, in particular, into parasympathetic neurons. The concentrations of BDNF and CNTF are preferably within a range of 40 to 100 ng/ml, respectively, and more preferably 100 ng/ml. Alternatively, instead of BDNF and CNTF, a BDNF signaling pathway activator and a CNTF signaling pathway activator having equivalent effects can be used. The culture conditions other than the composition of the culture medium may be the same as those of the differentiation induction culture in the section 2-1. Although the concentration of seeded neural crest cells may be the same as that in the section 2-2., a concentration lower than that in the section 2-2. is preferred because the proliferation of sympathetic neurons is suppressed. In particular, a concentration within a range of $5 \times 10^4$ to $1 \times 10^5$ cells/cm$^2$ is preferred.

According to this embodiment, the efficiency of inducing differentiation of neural crest cells into parasympathetic neurons can be increased four times or more compared to that when using a known culture medium (supplemented with 10 ng/ml BDNF, and not supplemented with CNTF) disclosed in the section 2-1. In the present specification, the efficiency of inducing differentiation of neural crest cells into parasympathetic neurons are a numerical value calculated based on the number of ChAT-positive cells. The ChAT-positive cells can be identified by, for example, immunostaining and can be counted.

(3. Regulation of Pluripotent Stem Cell-Derived Neural Crest Cells)

When pluripotent stem cell-derived neural crest cells are used, the method for inducing differentiation of pluripotent stem cells into neural crest cells can be a known method (e.g., the method described in Fukuta 2014). For example, culture can be performed using, for example, a DMEM/Ham's F-12 medium (Wako: 048-29785), human stem cell medium (hESM), or N-2 medium as the base medium in the presence of a combination of reagents selected from the group consisting of BMP signaling pathway inhibitors, TGF signaling pathway inhibitors, Wnt signaling pathway activators, FGF signaling pathway activators, and EGF signaling pathway activators.

Furthermore, the base medium can be appropriately supplemented with, for example, KSR, NEAA, monothioglycerol solution, P/S, or an N2 supplement.

Herein, the BMP signaling pathway inhibitor used in the step of inducing differentiation of pluripotent stem cells into neural crest cells can be a known compound, such as dorsomorphin (DM), LDN-193189, or noggin. The TGF signaling pathway inhibitor can be a known compound, such as SB431542 hydrate (SB). The Wnt signaling pathway activator can be a known compound, such as CHIR99021 (CHIR), Wnt-3a, or BIO. The FGF signaling pathway activator can be a known compound, such as a fibroblast growth factor (bFGF), and the EGF signaling pathway activator can be a known compound, such as an epidermal growth factor (EGF).

The concentration of DM as a BMP signaling pathway inhibitor supplemented to a culture medium is preferably within a range of 1 to 5 μM. The concentration of SB as an ALK inhibitor supplemented to a culture medium is preferably within a range of 1 to 20 μM. The concentration of CHIR as a GSK-30 inhibitor supplemented to a culture medium is preferably within a range of 1 to 6 μM. The concentration of bFGF as a growth factor supplemented to a culture medium is preferably within a range of 4 to 20 ng/ml.

The culture in such a method for inducing differentiation of pluripotent stem cells into neural crest cells is preferably performed for a period about 6 to 16 days. This culture step may be performed by an adherent culture method or by a floating culture method.

Each reagent can be appropriately selected without being limited to the above-mentioned examples, and the concentration of the reagent and the culture period can be appropriately determined depending on, for example, conditions of the reagents used in combination.

The method for inducing differentiation of pluripotent stem cells into neural crest cells can also be composed of two or more culture steps (e.g., two or three culture steps using culture media having different compositions). For example, as an embodiment, the method can be divided into two steps: a first culture step of performing culture with a medium supplemented with DM and SB for about 2 days; and a second culture step of subsequently performing culture with a medium supplemented with CHIR and SB for about 4 to 10 days. The present inventors have diligently researched and, as a result, have also found a more preferred embodiment of the method for inducing differentiation of pluripotent stem cells into neural crest cells. Such a more preferred embodiment in the present invention includes three steps: a first culture step of performing culture with a medium supplemented with DM, SB, and bFGF for about 2 days; a second culture step of performing culture, after the first culture step, with a medium supplemented with CHIR, SB, and bFGF for about 2 days; and a third culture step of performing culture, after the second culture step, with a medium supplemented with CHIR and bFGF for about 2 days. However, without being limited to these examples, the composition of each culture medium, the culture period with each medium, and the number of culture steps can be appropriately designed, with reference to the disclosure in the present specification and known methods, as long as pluripotent stem cells can be induced to differentiate into neural crest cells.

An example of the preferred embodiment found by the present inventors is more specifically composed of the following three steps.

That is, the embodiment can be implemented by a method composed of a first culture step of performing culture with an hESM medium supplemented with 2 μM DM, 10 μM SB, and 10 ng/ml bFGF for 2 to 3 days, preferably for 2 days; a second culture step of performing culture with an hESM medium supplemented with 3 μM CHIR, 20 μM SB, and 10 ng/ml bFGF for 1 to 3 days, preferably for 2 days; and a third culture step of performing culture with a medium mixture (3:1 (v/v)) of hESM supplemented with 3 μM CHIR and 10 ng/ml bFGF and N-2 medium for 1 to 3 days, preferably for 2 days. Such a combination of two or more culture steps is preferred because neural crest cells can be induced to differentiate into neurons with high differentiation induction efficiency. In addition, also in the method for inducing differentiation of pluripotent stem cells into neural crest cells, a combination of two or more culture steps as in above can regulate the differentiation induction of cells over time and can synchronize the differentiation stage of the cells during the culture. Such synchronization of the differentiation stage of the cells during the differentiation induction, as described above, allows the subsequent differentiation induction to be readily regulated (in other words, an appropriate compound can be utilized at an appropriate timing to easily obtain an expected effect) leading to an increase in the differentiation induction efficiency.

The method for inducing differentiation of pluripotent stem cells into neural crest cells is not limited to the above-mentioned examples and can be implemented by appropriately regulating the reagent to be used, its concentration, and the culture period. The method can be also implemented in accordance with a known method.

The pluripotent stem cells that are used in the method for inducing differentiation of the pluripotent stem cells into neural crest cells are preferably precultured by a known method under, for example, the following conditions.

That is, the preculture can be implemented by culturing pluripotent stem cells on a well coated with, for example, Geltrex, vitronectin, Matrigel, or laminin 511-E8 in a Y-27632-containing mTeSR1 medium for 2 to 3 days up to a confluent state. The confluent pluripotent stem cells can be used in the above-described method for inducing differentiation into neural crest cells.

Y-27632 is a Rho kinase (Rho-associated coiled-coil kinase: ROCK) inhibitor and is a reagent for suppressing dissociation-induced apoptosis when pluripotent stem cells are cultured. In the preculture, a reagent having equivalent effect may be used as an alternative. Y-27632 can be used at a concentration of, for example, 5 to 20 μM. The base medium to be used for preculture is also not limited to mTeSR1 and may be any culture medium for maintaining pluripotent stem cells.

In the culture for inducing pluripotent stem cells into neural crest cells, feeder cells may be used or may not be used.

Another aspect of the present invention provides a kit including a reagent for differentiating neural crest cells into neurons of the autonomic nervous system.

The kit of the present invention includes at least one agent selected from the group consisting of BMP signaling pathway activators, SHH signaling pathway inhibitors, and Wnt signaling pathway inhibitors. The BMP signaling pathway activator, the SHH signaling pathway inhibitor, and the Wnt signaling pathway inhibitor contained in the kit can be appropriately selected from the reagents mentioned above.

The kit of the present invention can also include a combination of, for example, a reagent and a culture well necessary for differentiating neural crest cells into neurons of the autonomic nervous system, in addition to the BMP signaling pathway activator, the SHH signaling pathway inhibitor, or the Wnt signaling pathway inhibitor. Furthermore, the kit of the present invention can also include a reagent necessary for inducing differentiation of pluripotent stem cells into neural crest cells (e.g., a BMP signaling pathway inhibitor, a TGF signaling pathway inhibitor, a Wnt signaling pathway activator, an FGF signaling pathway activator, or an EGF signaling pathway activator).

Furthermore, the kit of the present invention may include a document or manual describing the procedure of differentiation induction.

Examples

Examples of the present invention will now be described, but the present invention is not limited to these Examples.

Information on the reagents (reagent name, product number, manufacturer, abbreviation, etc.) used in the following Examples is as follows.

Used agents
mTeSR1 WO 2ME/MV (Stemcell Technologies: ST-05850G)—mTeSR1
DMEM/Ham's F-12 (Wako: 048-29785)
DMEM (high-glucose) (Wako: 043-30085)—DMEM
Opti-MEM (Life Technologies: 31985-070)
Fetal Bovine Serum (from Australia) (Wako: SFBS)—FBS
Knockout Serum Replacement (Life Technologies: 0828-028)—KSR
N2 supplement with transferrin (Apo) (Wako: 41-09041)—N2 supplement
MEM non-essential amino acids solution (Wako: 139-15651)—NEAA
Monothioglycerol solution (Wako: 95-15791)
Penicillin-streptomycin solution (Wako: 168-23191)—P/S
Brain Derived Neurotrophic Factor, Human, recombinant (Wako: 020-12913)—BDNF
Glial-cell Derived Neurotrophil Factor, Human, recombinant (Wako: 075-04153)—GDNF
Nerve Growth Factor-β, Human, recombinant (Wako: 41-07601)—NGF
Neurotrophin-3, Human, recombinant (Wako: 141-06643)—NT-3
L-ascorbic acid ester magnesium salt n-hydrate (Wako: 01319641)—ascorbic acid
Y-27632 (Wako: 253-00513)
Forskolin (Wako: 067-02191)—FSK
Dorsomorphin (Sigma-Aldrich: P5499-5MG)—DM
SB431542 hydrate (Sigma-Aldrich: S4317-5MG)—SB
CHIR99021 (Cayman Chemical Company: 13122)—CHIR
IWR-1 (Sigma-Aldrich: 10161-5MG)
SANT1 (Sigma-Aldrich: S4572-5MG)
Osteogenic factor 4 (truncated), human, recombinant (Wako: 022-17071)—BMP4
Fibroblast growth factor (basic) (basic FGF), human, recombinant (Wako: 064-04541)—bFGF
iMatrix-511 (Nippi: 892002)
Geltrex (hESC-qualified ready-to-use reduced growth factor basement membrane matrix) (Life Technologies: A15696-01)
Poly-L-ornithine hydrobromide (Sigma-Aldrich: P3655-10MG)—PLO
Laminin from Engelbreth-Holm-Swarm murine sarcoma basement membrane (Sigma-Aldrich: L2020-IMG)—Laminin
Accutase (Life Technologies: A11105-01)
TrypLE express (Life Technologies: 12604-013)
Ultrapure distilled water (Life Technologies: 10977-015)—DW
D-PBS(−) (Wako: 045-29795)—PBS
Tris Buffer Powder, pH 7.4 (Takara Bio: T9153)
Hydrochloric acid (Wako: 080-01066)
Albumin, from Bovine Serum (Wako: 017-23294)—BSA
Dimethyl sulfoxide (Wako: 074-29353)—DMSO
Formaldehyde solution (Wako: 064-00406)
10 w/v % polyoxyethylene (20) sorbitan monolaurate solution (Wako: 161-24801)—Tween-20
Block Ace Powder (DS Pharma Biomedical: UKB80)
Can Get Signal (solution 1&2) (TOYOBO: NKB-101)
Anti-beta III tubulin antibody (mouse monoclonal) (Abcam: AB7751)
Anti-Peripherin antibody (rabbit polyclonal) (Merck Millipore: AB1530)
Anti-Tyrosine Hydroxylase antibody (rabbit polyclonal) (Merck Millipore: AB152)
Hoechst 33342 solution (Dojindo: 346-07951)
F(ab')2-Goat anti-Mouse IgG (H+L) Secondary Antibody, Alexa Fluor® 488 conjugate (Life Technologies: A11017)—Alexa Fluor488
F(ab')2-Goat anti-Rabbit IgG (H+L) Secondary Antibody, Alexa Fluor® 555 conjugate (Life Technologies: A21430)—Alexa Fluor555
Ciliary Neurotrophic Factor, Human, recombinant (Wako: 032-18851)—CNTF
Anti-Tyrosine Hydroxylase (mouse monoclonal) (Merck Millipore: MAB318)
Anti-Choline Acetyltransferase (rabbit polyclonal) (Abcam: ab68779)
Lipidure CM-5206E (NOF)
Geneticin solution (Wako: 071-04971)

Regulation of Each Stock Solution
FSK: a 10 mM stock solution was produced using DMSO as the solvent.
DM: a 1 mM stock solution was produced using DMSO as the solvent.
SB: a 10 mM stock solution was produced using DMSO as the solvent.
CHIR: a 3 mM stock solution was produced using DMSO as the solvent.

IWR-1: a 10 mM stock solution was produced using DMSO as the solvent.

SANT1: a 250 µM stock solution was produced using DMSO as the solvent.

BMP4: a 100 sg/ml stock solution was produced using a 4 mM hydrochloric acid solution containing 0.1% BSA as the solvent.

bFGF: a 500 µg/ml solution was prepared using 1 mM Tris buffer (pH 7.4) as the solvent and then a 10 g/ml stock solution was produced using DMEM as the solvent.

BDNF, CNTF, GDNF, NGF, NT-3: a 10 µg/ml stock solution was produced using PBS as the solvent.

Ascorbic acid: a 50 mg/ml stock solution was produced using PBS as the solvent.

Y-27632: a 10 mM stock solution was produced using Opti-MEM as the solvent.

PLO: a 1 mg/ml stock solution was produced using DW as the solvent.

(i) Preparation of Human Stem Cell Medium (hESM) for Differentiation Induction

Human stem cell medium (hESM) was prepared such that DMEM/Ham's F-12 contains 20% (V/V) KSR, 1% (V/V) NEAA, 1% (V/V) monothioglycerol solution, and 1% (V/V) P/S (The concentration of each reagent is the final concentration).

(ii) Preparation of Medium (N-2 Medium) for Differentiation Induction and Nerve Culture N-2 medium was produced such that DMEM/Ham's F-12 contains 1% (V/V) N2 supplement, 1% (V/V) NEAA, and 1% (V/V) P/S.

(1-1. Preparation of Human iPS Cells for Differentiation Induction)

The human iPS cells (201B7 strain) used in the main test were distributed from RIKEN BioResource Center. The culture was performed using a 6-well plate (Corning: 3516). Coating treatment was performed by adding PBS to the plate at 1.5 ml/well and further adding iMatrix-511 (Nippi: 892002) to the plate at 0.5 µg/cm$^2$ and leaving the plate to stand for 1 hour. After the leaving to stand for 1 hour, the PBS solution was removed from each well, and mTeSR1 was added to the plate at 2 ml/well and further Y-27632 (×1000) was added to each well at a concentration of 10 µM to prepare a culture medium for human iPS cells.

In the culture solution for human iPS cells, (a) a frozen sample (frozen human iPS cells subjected thawing) or (b) subcultured human iPS cells were seeded at $4\times10^4$ to $1\times10^5$ cells/well. The human iPS cells were cultured under the conditions of 37° C. and 5% $CO_2$ (hereinafter, the culture of human iPS cells (including the culture in differentiation-inducing step) was performed under the same conditions). On the following day of the seeding, the culture medium was replaced by removing the supernatant of the culture medium and then adding mTeSR1 (without Y-27632) to each well. The culture medium was replaced every day from the following day of the seeding.

(1-2. Passage of Human iPS Cells)

During the culture of human iPS cells by the above-described method, human iPS cells reached semiconfluent were subcultured as follows.

First, mTeSR1 was removed from the well during the culture, and an accutase solution warmed to 37° C. was added to the plate at 1 ml/well, followed by incubation for 5 minutes. Subsequently, the accutase solution in each well was blown on the culture surface with a pipette to exfoliate the human iPS cells. The exfoliated human iPS cells were collected in a centrifuge tube. In order to collect the human iPS cells remaining in the well, 1 ml of PBS was added to the well, and the human iPS cells floating in the PBS were also collected in the centrifuge tube. The human iPS cells collected in the centrifuge tube were centrifuged at 200×g for 4 minutes. After the centrifugation, the supernatant was removed, followed by addition of 1 ml of mTeSR1 to suspend the human iPS cells. On this occasion, the cells in the suspension were counted.

The human iPS cells collected as described above were subcultured with a well plate coated with iMatrix described in the section 1-1, or were used in the differentiation induction treatment described below.

(2. Differentiation Induction into Autonomic Nervous System)

In order to induce differentiation of human iPS cells into the autonomic nervous system, human iPS cells for differentiation induction were prepared by the following preculture step.

For the preculture, a 12-well plate (Corning: 3513) was used. Geltrex was added to the well plate at 600 µL/well, followed by incubation at 37° C. for 1 hour. After the incubation, the Geltrex was removed, and an mTeSR1 solution containing 10 µM Y-27632 was added to the plate at 1 ml/well. Subsequently, the human iPS cells collected in the section 1-1, were seeded in the well plate at $4\times10^5$ to $6\times10^5$ cells/well. The human iPS cells were cultured under the conditions of 37° C. and 5% $CO_2$. The culture medium was replaced with mTeSR1 containing 10 µM Y-27632 every day from the following day of starting the culture, and the culture was continued for 2 to 3 days until the human iPS cells became confluent.

After the culture of the human iPS cells until confluent, the confluent human iPS cells were subjected to the treatment of the following differentiation-inducing steps 1 to 6 to induce differentiation of the human iPS cells into the autonomic nervous system.

In the following, as an embodiment, six steps are carried out. The following differentiation-inducing steps 1 to 3 correspond to a step of inducing differentiation of precultured pluripotent stem cells into neural crest cells. The following differentiation-inducing steps 4 and 5 correspond to a step of culturing neural crest cells while activating or inhibiting the signaling pathways (1) to (3). The following differentiation-inducing step 6 corresponds to a step of inducing differentiation of neural crest cells into neurons of the autonomic nervous system. The outline of this embodiment is shown in FIG. 1.

The differentiation-inducing method of the present invention is not limited to the embodiment.

Differentiation-Inducing Step 1

Preparation of Culture Medium for Use:

Each reagent was added to hESM such that 2 µM DM, 10 µM SB, and 10 ng/ml bFGF were contained to prepare a culture medium for differentiation-inducing step 1 (The concentration of each reagent is the final concentration. Hereinafter, the concentration of each reagent in preparation of a culture medium is shown as the final concentration.).

Culture Method:

From the well of confluent human iPS cells became confluent by the preculture, mTeSR1 containing 10 µM Y-27632 was removed. The culture medium for differentiation-inducing step 1 was added to the well. After the replacement with the culture medium for differentiation-inducing step 1, the culture was performed for 2 days.

Differentiation-Inducing Step 2
Preparation of Culture Medium for Use:
Each reagent was added to hESM such that 3 μM CHIR, 20 μM SB, and 10 ng/ml bFGF were contained to prepare a culture medium for differentiation-inducing step 2.
Culture Method:
After the culture in the differentiation-inducing step 1, the culture medium used for the differentiation-inducing step 1 was removed, and the culture medium for differentiation-inducing step 2 was added. After the replacement with the culture medium for differentiation-inducing step 2, the culture was performed for 2 days.
Differentiation-Inducing Step 3
Preparation of Culture Medium for Use:
As a base medium, a medium was produced by mixing hESM and N-2 medium at 3:1 (V/V). Subsequently, each reagent was added to the produced medium mixture such that 3 μM CHIR and 10 ng/ml bFGF were contained to prepare a culture medium for differentiation-inducing step 3.
Culture Method:
After the culture in the differentiation-inducing step 2, the culture medium used for the differentiation-inducing step 2 was removed, and the culture medium for differentiation-inducing step 3 was added. After the replacement with the culture medium for differentiation-inducing step 3, the culture was performed for 2 days.
Differentiation-Inducing Step 4
Preparation of Culture Medium for Use:
As a base medium, a medium was produced by mixing hESM and N-2 medium at 1:1 (V/V). Subsequently, each reagent was added to the produced medium mixture such that 10 μM IWR-1, 250 nM SANT1, 25 ng/mi BMP4, and 10 ng/ml bFGF were contained to prepare a culture medium for differentiation-inducing step 4.
Culture Method:
After the culture in the differentiation-inducing step 3, the culture medium used for the differentiation-inducing step 3 was removed, and the culture medium for differentiation-inducing step 4 was added. After the replacement with the culture medium for differentiation-inducing step 4, the culture was performed for 2 days.
Differentiation-Inducing Step 5
Preparation of Culture Medium for Use:
As a base medium, a medium was produced by mixing hESM and N-2 medium at 1:3 (V/V). Subsequently, each reagent was added to the produced medium mixture such that 10 μM IWR-1, 250 nM SANT1, 25 ng/ml BMP4, and 10 ng/ml bFGF were contained to prepare a culture medium for differentiation-inducing step 5.
Culture Method:
After the culture in the differentiation-inducing step 4, the culture medium used for the differentiation-inducing step 4 was removed, and the culture medium for differentiation-inducing step 5 was added. After the replacement with the culture medium for differentiation-inducing step 5, the culture was performed for 4 days (after the culture for 2 days, the whole culture medium for differentiation-inducing step 5 was replaced with a fresh one).
Differentiation-Inducing Step 6
Preparation of Culture Well Plate:
A 24-well plate was coated with a 50-fold diluted PLO (20 μg/ml). The coating treatment was performed in an incubator for 1 hour. After the coating treatment, the PLO solution was removed, and the well plate was washed with DW once. After the washing of the well plate, coating treatment with a 20-fold diluted laminin (5 μg/ml) was carried out. The coating treatment was performed in an incubator for 2 hours.

The well plate thus-coated with PLO and laminin was used for the culture in the differentiation-inducing step 6.
Preparation of Culture Medium (Neural Differentiation Medium (NDM)) for Use:
Each reagent was added to N-2 medium such that 10 μM FSK, 10 ng/ml BDNF, 10 ng/ml GDNF, 10 ng/ml NT-3, 10 ng/ml NGF, and 50 μg/ml ascorbic acid were contained to prepare a culture medium (NDM) for differentiation-inducing step 6.
Culture:
After the culture in the differentiation-inducing step 5, the culture medium used for the differentiation-inducing step 5 was removed, and PBS was added for washing once. After the washing with PBS, TrypLE express was added at 250 μL/well, followed by incubation at 37° C. for 5 minutes. DMEM containing 10% FBS was then added at 1 ml/well to stop the enzyme reaction, and the cultured cells were exfoliated from the well plate and were collected in a centrifuge tube. The cells collected in the centrifuge tube were centrifuged at 200×g for 4 minutes. After the centrifugation, the supernatant was removed, followed by addition of NDM to suspend the cells. After the suspension, apart of the NDM solution suspending the cells was sampled, and the cells therein were counted. Based on the information on the resulting number of the cells, the cells were seeded in a 24-well plate coated with PLO and laminin at a concentration of $1\times10^5$ to $2.5\times10^5$ cells/well. After seeding, a half amount of the NDM was replaced with a fresh one at a frequency of twice a week during the culture. The culture of the differentiation-inducing step 6 was performed for 23 days, and differentiation into the autonomic nervous system was induced. In order to confirm differentiation into the autonomic nervous system, the sample after 23 days was subjected to an immunostaining experiment as described in the following Example.
(3. Immunostaining)
The sample after the differentiation induction culture in the section 2 was washed with a PBS solution once. Subsequently, fixing treatment was performed in PBS containing 3.7% formaldehyde for 20 minutes. After the fixing treatment, the sample was washed with PBS once and incubated with a PBS solution containing 0.2% Tween-20 for 5 minutes. Subsequently, the PBS solution containing Tween-20 was removed, and blocking treatment was performed with a 4% Block Ace solution (prepared by dissolving 4% (w/v) Block Ace Powder in a PBS solution containing 0.2% Tween-20) for 30 minutes. After the blocking treatment, washing with a PBS solution containing 0.2% Tween-20 was performed once. After the washing, a Can Get Signal 1 solution containing a primary antibody was added to the well plate, and the well plate was left to stand at 4° C. overnight.
The primary antibodies and their dilution concentrations used were as follows:
(i) anti-TUJ1 antibody 1:1000 dilution
(ii) anti-peripherin antibody 1:1000 dilution
(iii) anti-TH antibody 1:500 dilution
After a primary antibody reaction by leaving to stand overnight, the Can Get Signal 1 solution was removed, followed by washing with a PBS solution containing 0.2% Tween-20 twice. After the washing, a Can Get Signal 2 solution containing a secondary antibody was added to the well plate, and the well plate was left to stand for 1 hour.
The secondary antibodies and their dilution concentrations used were as follows:
(i) Alexa Fluor488 1:1000 dilution
(ii) Alexa Fluor555 1:000 dilution
(iii) Hoechst 33342 1:3000 dilution After reaction treatment with a secondary antibody, washed twice with a PBS solution containing 0.2% Tween-20, observation and photographing with a fluorescence microscope were performed.

Figure 2A:
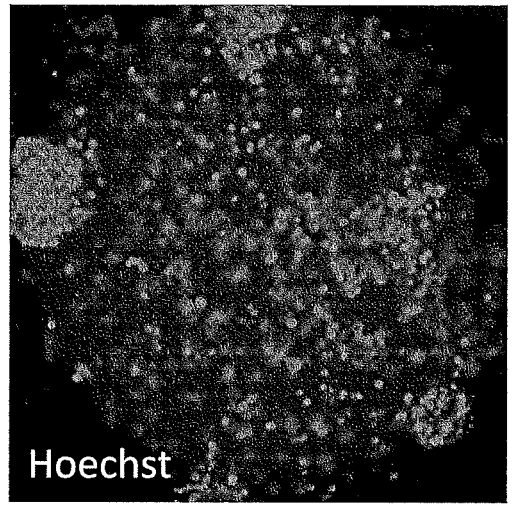
FIG. 2(a) shows an image of the cells stained with Hoechst 33342.
Figure 2B:
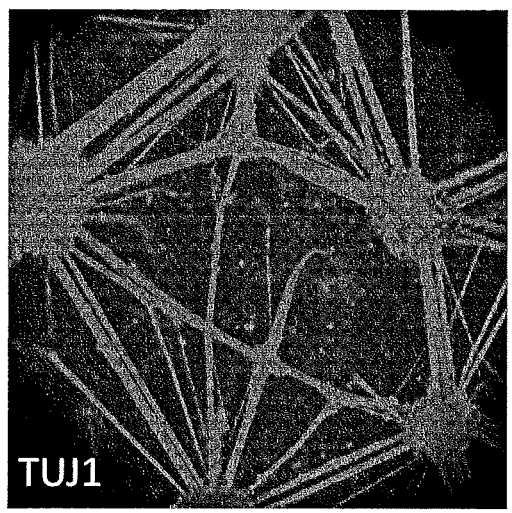
FIG. 2(b) shows an image of the cells stained with an antibody (anti-TUJ1 antibody) against a (beta) III tubulin (TUJ1)
Figure 2C:
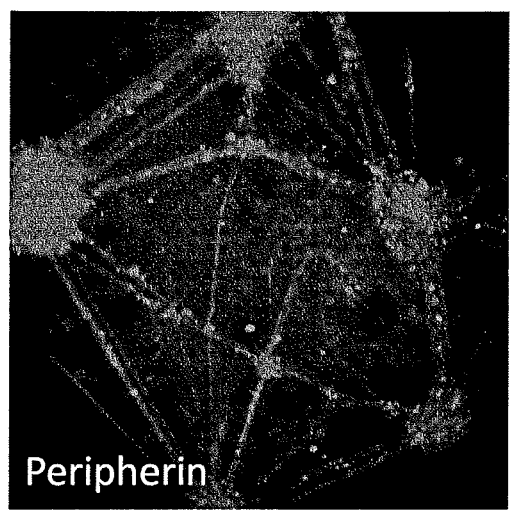
FIG. 2(c) shows an image of the cells stained with an anti-peripherin antibody.
Figure 3A:
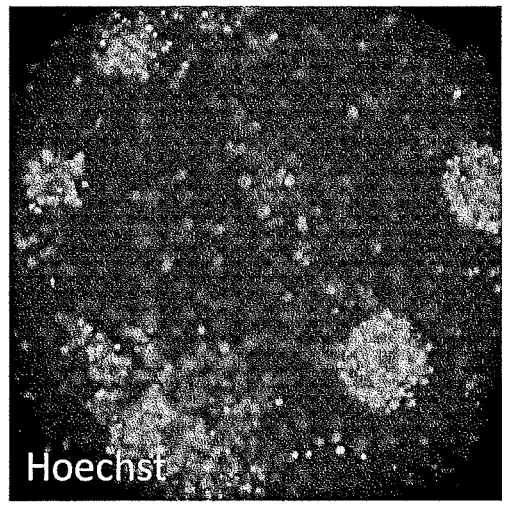
FIG. 3(a) shows an image of the cells stained with Hoechst 33342.
Figure 3B:
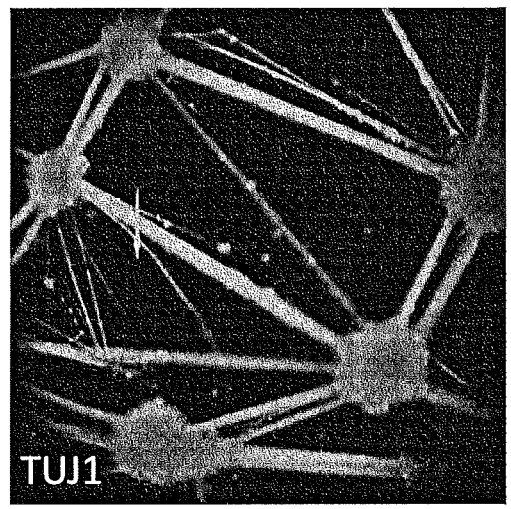
FIG. 3(b) shows an image of the cells stained with an anti-TUJ1 antibody.
Figure 3C:
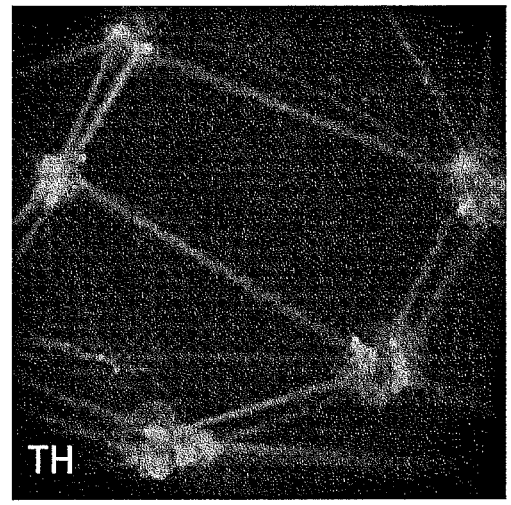
FIG. 3(c) shows an image of the cells stained with an anti-tyrosine hydroxylase antibody.

The results are shown in FIGS. 2 and 3. FIG. 2 shows the results of double staining using an anti-TUJ1 antibody and an anti-peripherin antibody as primary antibodies. As shown in FIG. 2, in a sample derived from human iPS cells treated by the method of the section "2. Differentiation induction into autonomic nervous system" (hereinafter, referred to as "differentiation-inducing method (b)"), TUJ1-positive cell population, where TUJ1 is a differentiation marker for neurons, was obtained. Furthermore, according to FIG. 2, in the sample derived from human iPS cells treated by the differentiation-inducing method (b), response of peripherin-positive cell population was also observed. Peripherin is known as a marker protein for peripheral neurons. Accordingly, the results of FIG. 2 reveal that human iPS cells were differentiated into peripheral neurons by the differentiation induction treatment.

FIG. 3 shows the results of double staining using an anti-TUJ1 antibody and an anti-TH antibody as primary antibodies. As shown in FIG. 3, in a sample derived from human iPS cells treated by the differentiation-inducing method (b), TH1-positive cell population was observed. TH is known as a marker protein for neurons of the autonomic nervous system. Accordingly, the results of FIG. 3 reveal that human iPS cells were differentiated into neurons of the autonomic nervous system by the differentiation induction treatment.

(4. Evaluation of Differentiation Induction Efficiency)

In order to evaluate the differentiation induction efficiency of the differentiation-inducing method of the present invention, differentiation induction into neurons of the autonomic nervous system was performed by a known method (hereinafter, referred to as "differentiation-inducing method (a)") or the differentiation-inducing method (b), and the differentiation induction efficiencies of the respective methods were evaluated and compared.

Figure 4:
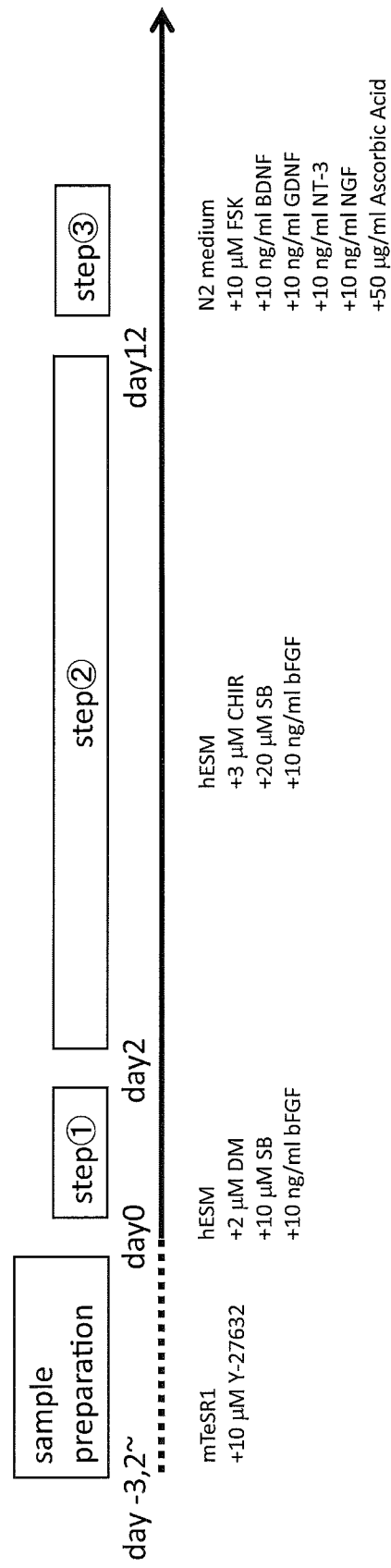
FIG. 4 is a diagram showing a known method for differentiating pluripotent stem cells into neurons of the peripheral nervous system. This method includes a pluripotent stem cell-preculturing step and three cell-culturing steps, and the composition of the culture medium and the number of culture days in each of the culturing steps is disclosed.

The outline of the differentiation-inducing method (a) is, as shown in FIG. 4, composed of a step for preculturing iPS cells and the following three differentiation-inducing steps A to C.

More specifically, as the preculture, human iPS cells ($4 \times 10^5$ to $6 \times 10^5$ cells/well) obtained by the method described in the section "1-1. Preparation of human iPS cells for differentiation induction" were cultured using a 12-well plate (Corning: 3513) coated with Geltrex in the presence of an mTeSR1 solution containing 10 μM Y-27632, as in the differentiation-inducing method (b). The culture was performed under the conditions of 37° C. and 5% $CO_2$. The culture medium was replaced with mTeSR1 containing 10 μM Y-27632 every day from the following day of starting the culture, and the culture was continued for 2 to 3 days until the human iPS cells became confluent.

After the culture of the human iPS cells up to a confluent state, the confluent human iPS cells were subjected to the treatment of the differentiation-inducing step shown below to induce differentiation of the human iPS cells into the autonomic nervous system.

Differentiation-Inducing Step A
Preparation of Culture Medium for Use:
Each reagent was added to hESM such that 2 μM DM, 10 μM SB, and 10 ng/ml bFGF were contained to prepare a culture medium for differentiation-inducing step A.

Culture Method:
From the well of human iPS cells became confluent by the preculture, mTeSR1 containing 10 μM Y-27632 was removed. The culture medium for differentiation-inducing step A was added to the well. After the replacement with the culture medium for differentiation-inducing step A, the culture was performed for 2 days.

Differentiation-Inducing Step B
Preparation of Culture Medium for Use:
Each reagent was added to hESM such that 3 μM CHIR, 20 $s^1$M SB, and 10 ng/ml bFGF were contained to prepare a culture medium for differentiation-inducing step B.

Culture Method:
After the culture in the differentiation-inducing step A, the culture medium for differentiation-inducing step A was removed, and the culture medium for differentiation-inducing step B was added. After the replacement with the culture medium for differentiation-inducing step B, the culture was performed for 10 days. The entire culture medium was replaced with fresh medium every 2 days.

Differentiation-Inducing Step C
Preparation of Culture Well Plate:
A 24-well plate was coated with 50-fold diluted PLO (20 μg/ml). The coating treatment was performed in an incubator for 1 hour. After the coating treatment, the PLO solution was removed, and the well plate was washed with DW once. After the washing of the well plate, coating treatment with a 20-fold diluted laminin (5 μg/ml) was carried out. The coating treatment was performed in an incubator for 2 hours. The well plate thus-coated with PLO and laminin was used for the culture in the differentiation-inducing step C.

Preparation of Culture Medium (Neural Differentiation Medium (NDM)) for Use:
Each reagent was added to N-2 medium such that 10 μM FSK, 10 ng/ml BDNF, 10 ng/ml GDNF, 10 ng/ml NT-3, 10 ng/ml NGF, and 50 μg/ml ascorbic acid were contained to prepare a culture medium (NDM) for differentiation-inducing step C.

Culture:
After the culture in the differentiation-inducing step B, the culture medium for differentiation-inducing step B was removed, and PBS was added for washing once. After the washing with PBS, TrypLE express was added at 250 μL/well, followed by incubation at 37° C. for 5 minutes. DMEM containing 10% FBS was then added at 1 ml/well to stop the enzyme reaction, and the cultured cells were exfoliated from the well plate and were collected in a centrifuge tube. The cells collected in the centrifuge tube were centrifuged at 200×g for 4 minutes. After the centrifugation, the supernatant was removed, followed by addition of NDM to suspend the cells. After the suspension, a part of the NDM solution suspending the cells was sampled, and the cells therein were counted. Based on the information on the resulting number of the cells, the cells were seeded in a 24-well plate coated with PLO and laminin at a concentration of $1 \times 10^5$ to $2.5 \times 10^5$ cells/well. After the seeding, half the amount of the NDM was replaced with fresh at a frequency of twice a week during the culture. The culture of the differentiation-inducing step C was performed for 23 days, and differentiation into the autonomic nervous system was induced.

The thus-obtained cells were used in immunostaining for evaluating the differentiation induction efficiency into neurons of the autonomic nervous system by the known differentiation-inducing method (a).

In order to evaluate the induction efficiency of the differentiation-inducing method of the present invention, the cells obtained by the differentiation-inducing method (a) or the differentiation-inducing method (b) were immunostained. The immunostaining was performed as in the method described in the section 3, except that an anti-TUJ1 antibody and an anti-TH antibody were used.

Figure 5A:
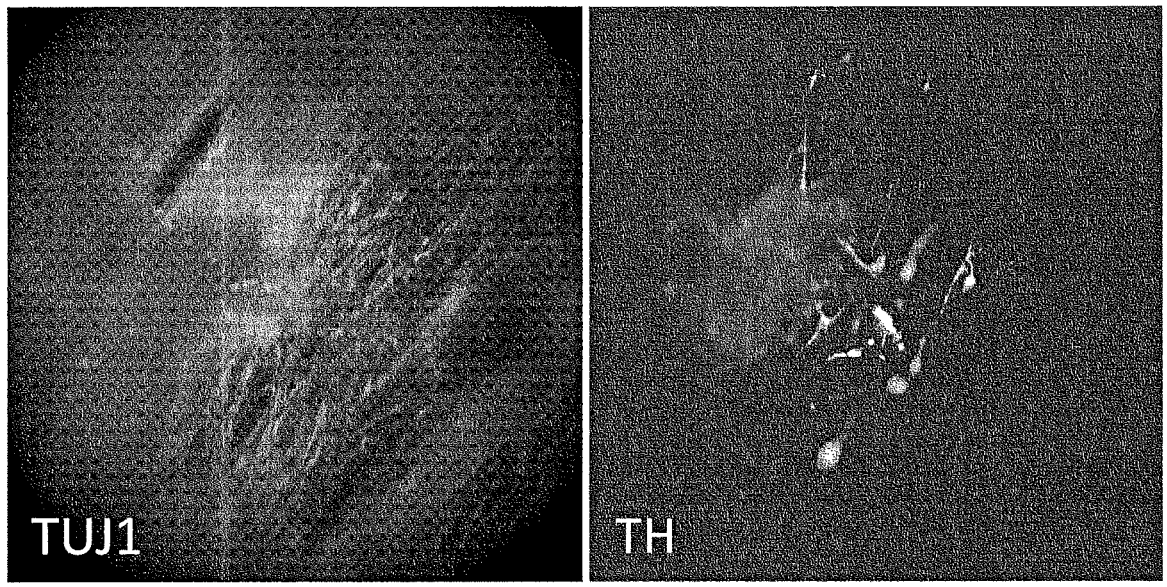
FIG. 5 shows images, taken under a fluorescence microscope, of cells differentiated by a known method for inducing differentiation of pluripotent stem cell-derived neural crest cells into neurons of the peripheral nervous system (FIG. 5(a)) or cells differentiated by the method described in "2. Differentiation induction into autonomic nervous system" in the following Example (FIG. 5(b)), each immunostained with an anti-TUJ1 antibody and an anti-tyrosine hydroxylase (TH) antibody.
Figure 5B:
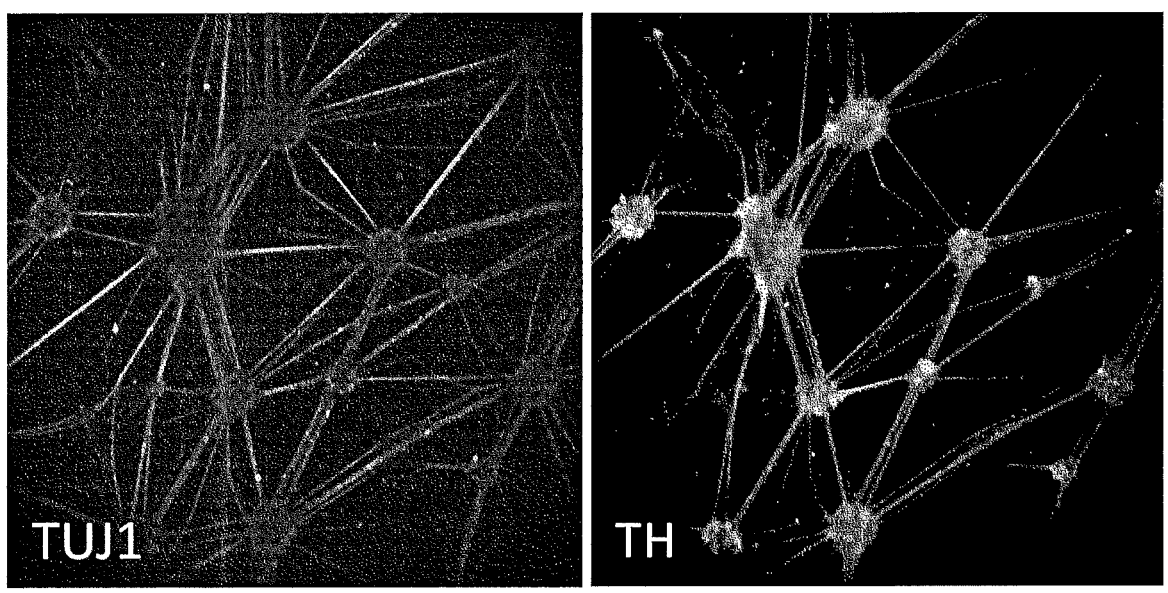

FIG. 5 shows the results of the immunostaining. As shown in FIG. 5(a), although most of the cells obtained by the differentiation-inducing method (a) were TUJ1 positive, the cells were dispersively grafted as a whole to form a mesh-like circuit network. Among the cells obtained by the differentiation-inducing method (a), only few cells were TH positive. In contrast, as shown in FIG. 5(b), the cells obtained by the differentiation-inducing method (b) were crowded together to form cell aggregates, and most of the cells were TUJ1 positive. In many of the cells obtained by the differentiation-inducing method (b), TH was positive. The cells were counted with ImageJ software, and the differentiation induction efficiency of each differentiation-inducing method was evaluated by dividing the number of TH-positive cells by the number of TUJ1-positive cells. As a result, the differentiation induction efficiency of the differentiation-inducing method (b) was 63.0±11.8%, whereas the differentiation induction efficiency of the differentiation-inducing method (a) was 2.0±1.3% (FIG. 6). Thus, the differentiation-inducing method of the present invention induced neurons of the autonomic nervous system with a high efficiency.

(5. Functional Evaluation of Neurons of the Autonomic Nervous System Obtained by Differentiation Induction)

In order to investigate whether the neurons of the autonomic nervous system obtained by the differentiation-inducing method of the present invention matured to functional neurons or not, the function was evaluated by calcium imaging. In the test for the evaluation, the cells induced differentiation by the differentiation-inducing method (b) (the cells on the 35th culture day in the differentiation-inducing step 6) were used.

More specifically, the functional evaluation by calcium imaging was performed as follows.

A calcium probe, fluo-4/AM (Invitrogen: F14201), was dissolved in DMSO to prepare 1 mg/ml fluo-4/AM solution. The cells obtained by the differentiation-inducing method (b) (where the differentiation-inducing step 6 was carried out for 35 days) were used, and the fluo-4/AM solution (fluo-4/AM solution diluted by 200-fold) was directly added to the culture medium for differentiation-inducing step 6 at 5 μg/ml. After the addition of the fluo-4/AM solution to the culture medium, incubation in an incubator (37° C., 5% $CO_2$) was carried out for 30 minutes. After the incubation, the culture medium containing fluo-4/AM was replaced with Ringer's solution (149 mM NaCl, 2.8 mM KCl, 2 mM $CaCl_2$, 1 mM $MgCl_2$, 10 mM HEPES, 10 mM D-(+)-glucose, pH 7.4), followed by fluorescence observation. In the fluorescence observation, 300 frames were photographed under a condition of 2 fps (frames per second) using an Olympus microscope (IX81), EM-CCD (Andor iXon+), and Metamorph software (Molecular Devices).

A platinum electrode (diameter: 0.5 mm, The Nilaco Corporation) was inserted into the measurement sample solution, and electric stimulation was applied with an electric stimulation apparatus (Nihon Kohden Corporation: SEN-3401). As the electric stimulation, a cathodic pulse (10 V amplitude, 3 ms width) was applied.

FIG. 7 shows the results. FIG. 7(a) shows a phase contrast image, and FIG. 7(b) is an image showing calcium fluorescence intensity immediately after the application of the electric stimulation. As shown in FIG. 7(b), strong calcium fluorescence intensity by the electric stimulation was observed only at a neurons of the autonomic nervous system site in the central portion of the image. This result revealed that the neurons of the autonomic nervous system induced by the differentiation-inducing method of the present invention are activated by the electric stimulation.

Figure 8A:
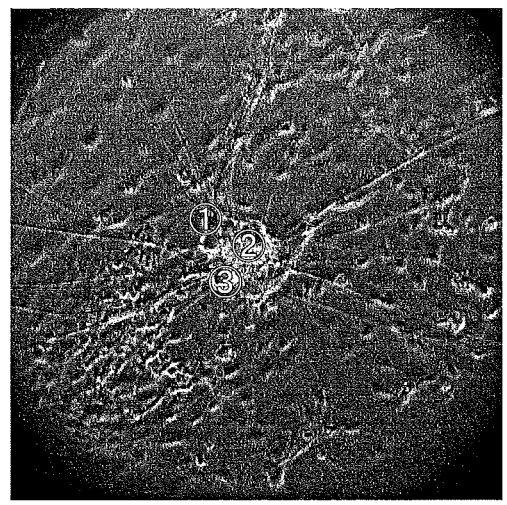
FIG. 8(a) is the same phase contrast image as in FIG. 7(a) and is an image specifying the cells used for this test.
Figure 8B:
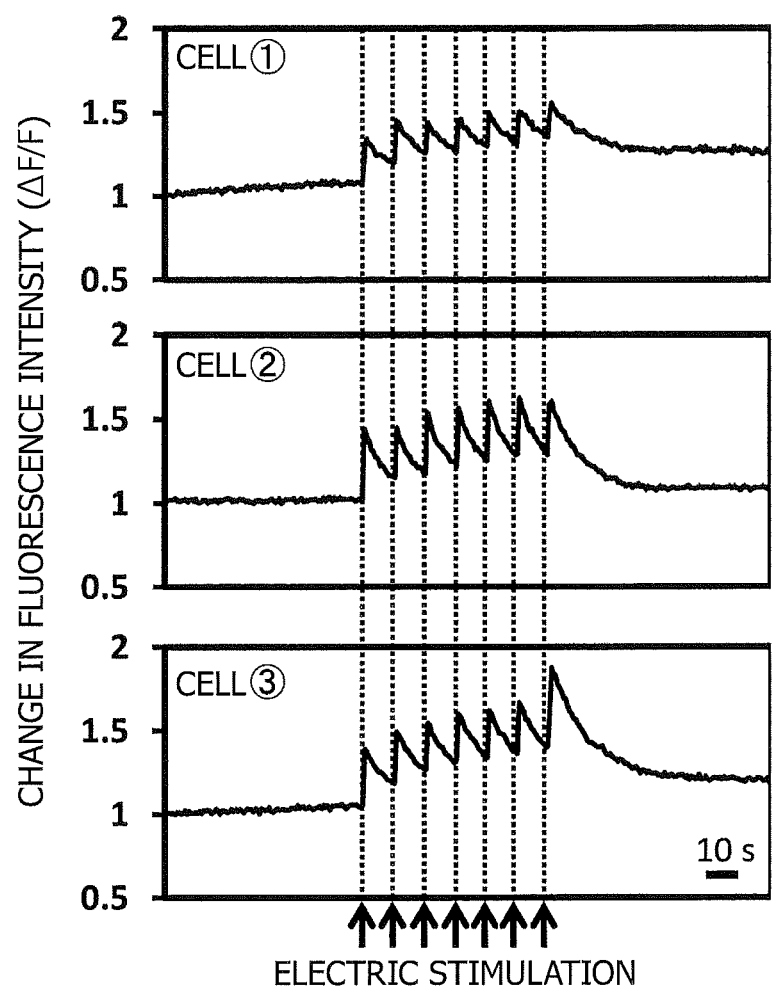
FIG. 8(b) shows graphs plotting fluorescence intensity over time when electric stimulation was applied multiple times.

Three neurons were selected from the phase contrast image shown in FIG. 7 (see FIG. 8(a)), and changes in calcium fluorescence intensity by electric stimulation seven times (application of a pulse of 10 V amplitude and 3 ms width seven times at intervals of 10 s) were observed over time. The data measured during the electric stimulation was analyzed with ImageJ. The results are shown in FIG. 8(b). It was revealed that spontaneous cell activity was not observed before and after the application of electric stimulation, but cell activity occurred as a response to electric stimulation.

Such characteristics that spontaneous activity was not basically observed and cell activity occurred in response to external stimulation, such as electric stimulation, are similar to the characteristics observed in cultured neurons of the autonomic nervous system collected from a rat (see Schorge, et al., Nature Neurosci. 2(9): 785-790 (1999); Takeuchi, et al., Lab Chip 11: 2268-2275 (2011)).

These results suggest that neurons of the autonomic nervous system induced by the differentiation-inducing method of the present invention are differentiated and matured to functional neurons.

The method for inducing differentiation into neurons of the autonomic nervous system described in Examples above and functionality of neurons of the autonomic nervous system obtained by the differentiation induction were evaluated by similar tests using human iPS cell 253G1 strain and our own human iPS cell strain. As a result, induction to the autonomic nervous system at efficiencies similar to that in 201B7 strain was observed. As in 201B7 strain, characteristics that cell activity occurs in response to electric stimulation were observed.

It was also confirmed that even when the differentiation-inducing method (b) was performed by floating culture, similarly, differentiation induction into neurons of the autonomic nervous system is possible with a high efficiency.

In the preculture by floating culture, a 6-well plate was used. The wells were coated with a small amount (about 100 μL/well) of Lipidure-CM5206E and were dried in a clean bench for 1 hour. The plate was then washed with PBS once, and mTeSR1 containing 10 μM Y-27632 was added to the plate at 2 ml/well. Subsequently, the human iPS cells collected in the section 1-1, were seeded at $1 \times 10^6$ to $2 \times 10^6$ cells/well. The culture medium was replaced with mTeSR1 containing 10 μM Y-27632 every day from the following day of starting the culture, and the culture was continued for 3 days.

After the differentiation-inducing step 5 by floating culture, the cultured cells were collected in a centrifuge tube. After centrifugation, the supernatant was removed, and 1 ml of TrypLE express was added to the residue, followed by incubation at 37° C. for 10 minutes.

The cells were cultured under the same conditions as those in the adherent culture, except the above.

(6. Induction of Selective Differentiation into Sympathetic Neurons)

The differentiation-inducing method (b) was performed as in above except that the cell-seeding concentration in the differentiation-inducing step 6 was $5 \times 10^4$ cells/cm$^2$, $1 \times 10^5$ cells/cm$^2$, or $2 \times 10^5$ cells/cm$^2$, and the differentiation induction efficiencies into sympathetic neurons were compared. The cells on the 43rd culture day in the differentiation-inducing step 6 were evaluated for the differentiation induction efficiency by investigating the expression of a sympathetic neuron marker, TH, by immunostaining. The immunostaining was performed as in the method described in the section 3, except that an anti-TH antibody was used.

Figure 10:
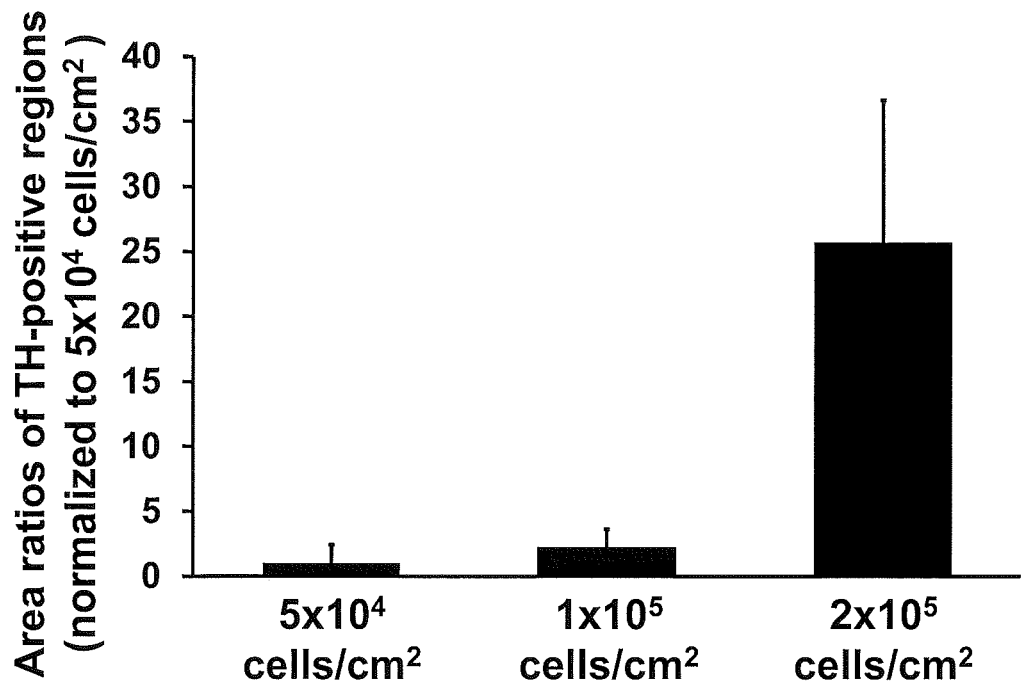
FIG. 10 is a graph showing differentiation induction efficiency into sympathetic neurons when the cell-seeding concentration was changed in the differentiation-inducing step 6 in the following Example.

FIG. 9 shows the results of the immunostaining. An increase in the appearance ratio of TH-positive cells was observed when the differentiation was induced at a cell-seeding concentration of $2\times10^5$ cells/cm$^2$. FIG. 10 shows area ratios of TH-positive regions in differentiation induction at various cell-seeding concentrations to that in differentiation induction at a cell-seeding concentration of $5\times10^4$ cells/cm$^2$. Although the appearance ratio of TH-positive cells scarcely changed when the cell-seeding concentration was $1\times10^5$ cells/cm$^2$, the appearance ratio of TH-positive cells increased by about 25 times at $2\times10^5$ cells/cm$^2$. These results demonstrate that the differentiation induction efficiency into sympathetic neurons is increased by performing the differentiation-inducing step 6 at a cell-seeding concentration of $2\times10^5$ cells/cm$^2$ or more.

(7. Induction of Selective Differentiation into Parasympathetic Neurons)

The differentiation-inducing method (b) was performed as above except that the following NDM2 was used instead of NDM or NDM as the culture medium in the differentiation-inducing step 6 and the cell-seeding concentration in the differentiation-inducing step 6 was $5\times10^4$ cells/cm$^2$, and the differentiation induction efficiencies into parasympathetic neurons were compared.

Culture Medium for Use (Neural Differentiation Medium (NDM2)):

Each reagent was added to N-2 medium such that 10 μM FSK, 100 ng/ml BDNF, 100 ng/ml CNTF, 10 ng/ml GDNF, 10 ng/ml NT-3, 10 ng/ml NGF, and 50 μg/ml ascorbic acid were contained.

The cells on the 20th culture day in the differentiation-inducing step 6 were evaluated for the differentiation induction efficiency by investigating the expression of a parasympathetic neuron marker, choline acetyltransferase (ChAT), by immunostaining. The immunostaining was performed as in the method described in the section 3, except that an anti-ChAT antibody was used.

Figure 11A:
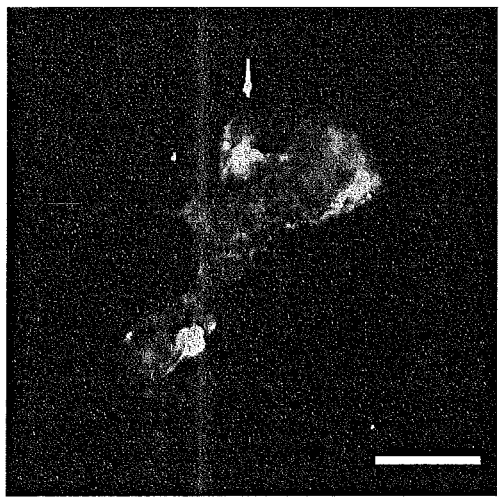
FIG. 11 shows images, taken under a fluorescence microscope, of cells subjected to differentiation induction using a culture medium (a) NDM or (b) NDM2 in the differentiation-inducing step 6 in the following Example and immunostained with an anti-ChAT antibody.
Figure 11B:
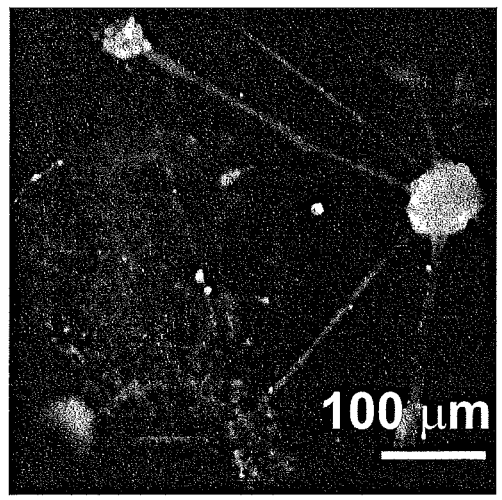

FIG. 11 shows the results. It was demonstrated that the number of ChAT-positive cells was increased by culture with NDM2 (FIG. 11(b)) compared to the culture with NDM (FIG. 11(a)).

Subsequently, in order to investigate the influence of the cell-seeding concentration on differentiation induction into parasympathetic neurons, induction differentiation as above was performed at a cell-seeding concentration of $5\times10^4$ cells/cm$^2$, $1\times10^5$ cells/cm$^2$, or $2.5\times10^5$ cells/cm$^2$, and the differentiation induction efficiencies into parasympathetic neurons were compared. The differentiation induction efficiencies were compared by comparing the numbers of ChAT-positive cells per unit area.

Figure 12:
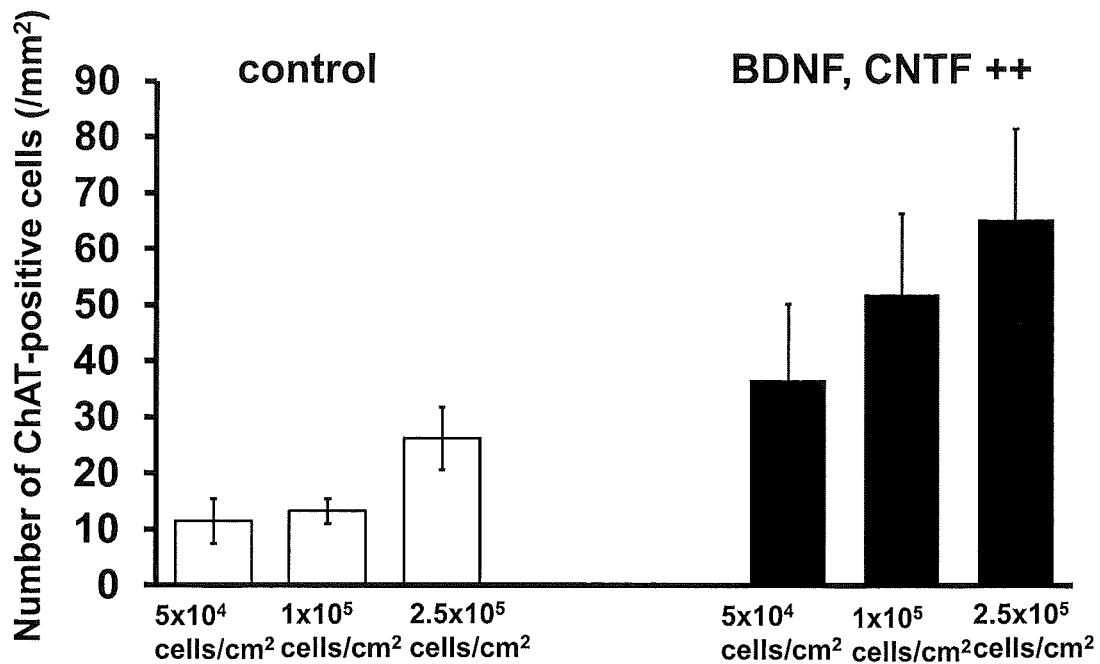
FIG. 12 is a graph showing differentiation induction efficiency into parasympathetic neurons when the cell-seeding concentration was changed in the differentiation-inducing step 6 in the following Example.
Figure 13:
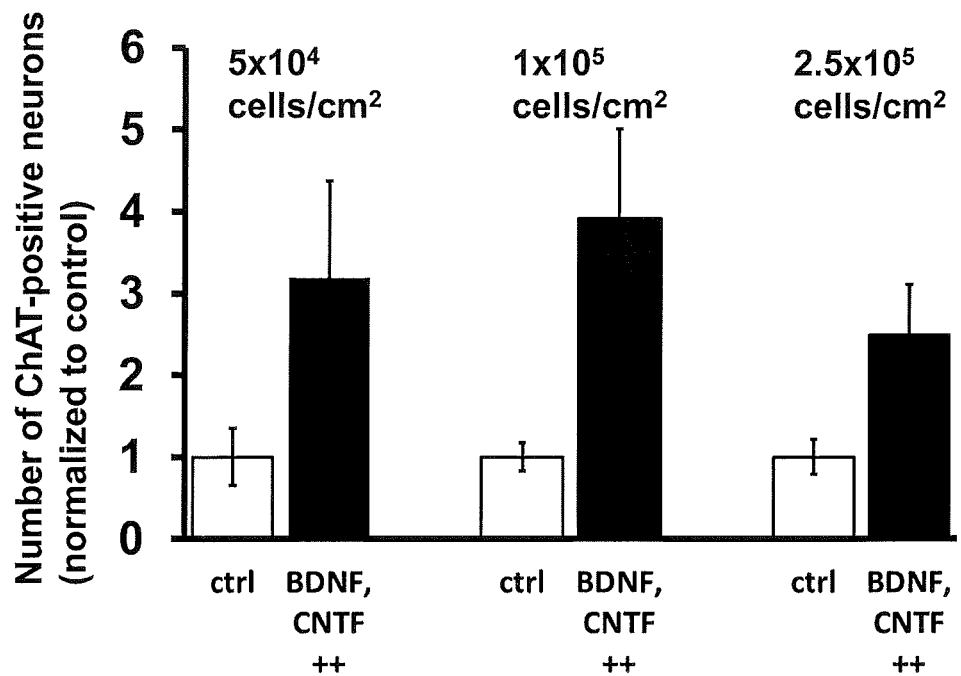
FIG. 13 is a graph showing differentiation induction efficiency into parasympathetic neurons when the medium composition was changed in the differentiation-inducing step 6 in the following Example.

FIG. 12 shows the results. It was demonstrated that the influence of the cell-seeding concentration on the differentiation induction efficiency is small even when either NDM or NDM2 is used as the culture medium. FIG. 13 shows the results of comparison of the differentiation induction efficiencies by NDM or NDM2 at each cell-seeding concentration. At every cell-seeding concentration, the number of ChAT-positive cells was increased when NDM2 was used (FIG. 13, BDNF, CNTF++) by 2 to 4 times compared to that when NDM was used (FIG. 13, ctrl). These results suggest that the differentiation induction efficiency into parasympathetic neurons is increased by adding BDNF and CNTF to the culture medium in the differentiation-inducing step 6.

(8. Purification of Neurons of the Autonomic Nervous System)

Figure 14A:
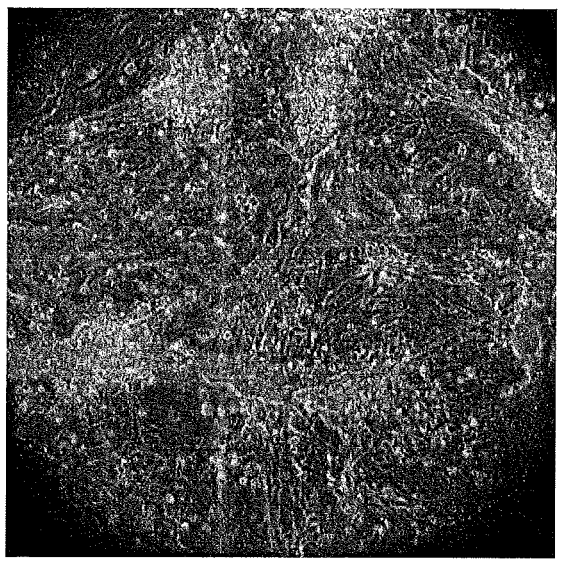
FIG. 14 includes (a) a phase contrast image and (b) a GFP fluorescence image of cells transfected with a drug resistance gene after the differentiation-inducing step 6 in the following Example.
Figure 14B:
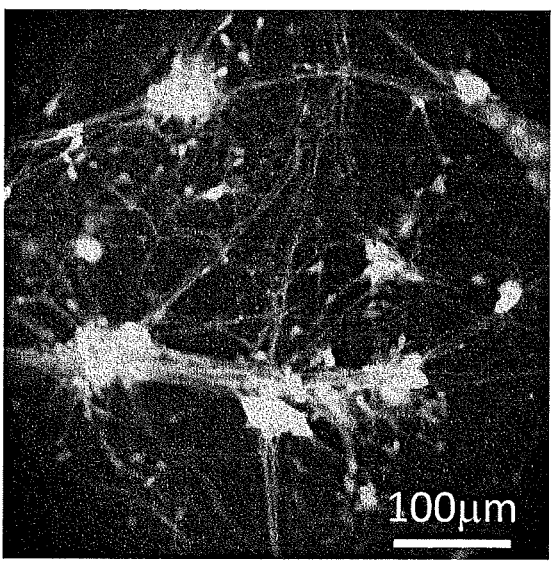
Figure 15A:
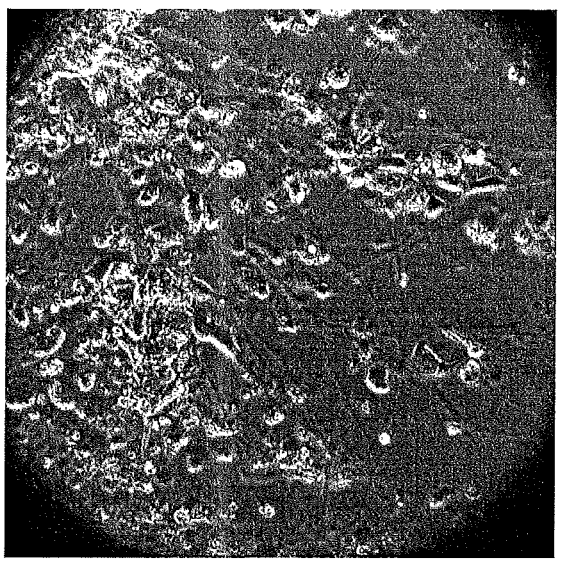
FIG. 15 includes (a) a phase contrast image and (b) a GFP fluorescence image of cells subjected to drug selection culture after the differentiation-inducing step 6 in the following Example.
Figure 15B:
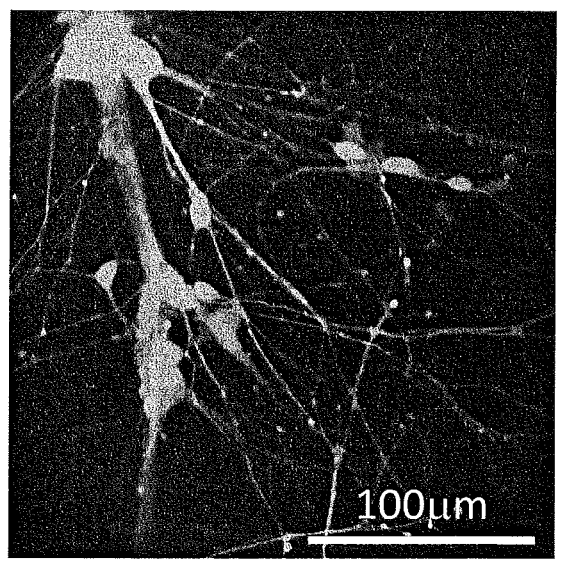

The differentiated autonomic nerve cells were purified by a drug resistant method in accordance with a known method (Zhou, Z., et al., Mol. Brain, 7:24). In a brief description, the cells on the 20th day in the differentiation-inducing step 6 were infected with a Lentiviral vector incorporated with GFP and a neomycin-resistant gene downstream the synapsin gene promoter. On the 4th day from the virus infection, expression of the gene introduced by the virus infection was observed by GFP fluorescence observation (FIG. 14). Subsequently, the culture medium was replaced with a culture medium containing 800 μg/ml Geneticin. After the culture for 2 days, it was observed that only the cells expressing GFP survived (FIG. 15).

The cells after the selective culture were evaluated for the expression levels of a peripheral neuron marker (peripherin), a neurons of the autonomic nervous system marker (Phox2b), a sympathetic neuron marker (TH), and a parasympathetic neuron marker (ChAT). The quantitative PCR was performed in accordance with the method described in the manuals attached to the used reagents and kit (ReliaPrep RNA Cell miniprep system (Promega), ReverTra Ace qPCR RT kit (TOYOBO), and THUNDERBIRD SYBR qPCR Mix (TOYOBO)).

FIG. 16 shows the results. It was observed that the expressions of all the marker genes were increased, compared to those when the purification was not performed. This result demonstrates that sympathetic neurons and/or parasympathetic neurons can be obtained with a higher efficiency by further combining a method for purifying neurons of the autonomic nervous system with the differentiation-inducing method of the present invention.

The invention claimed is:

1. A differentiation-inducing method for producing neurons of the autonomic nervous system from neural crest cells, the method comprising the steps of:
    (a) culturing the neural crest cells for 5 to 7 days in a culture medium comprising hESM, N-2 medium or a mixture thereof in the presence of a combination of a BMP signaling pathway activator, SHH signaling pathway inhibitor, and Wnt signaling pathway inhibitor; wherein the BMP signaling pathway activator is at least one BMP signaling pathway activator selected from the group consisting of BMP2, BMP4, BMP7, and BMP2/4 in an amount within a range of 0.1 ng/ml to 100 ng/ml; wherein the SHH signaling pathway inhibitor is at least one SHH signaling pathway inhibitor selected from the group consisting of SANT, JK184, and Jervine in an amount within a range of 20 nM to 2 μM; and wherein the Wnt signaling pathway inhibitor is at least one Wnt signaling pathway inhibitor selected from the group consisting of IWR, XAV939, and IWP in an amount within a range of 0.5 μM to 100 μM; and
    (b) culturing the cells produced from step (a) for 10 to 30 days in a culture medium comprising N-2 medium in the presence of a combination of a cAMP production promoter, a BDNF signaling pathway activator, a GDNF signaling pathway activator, an NGF signaling pathway activator, an NT-3 signaling pathway activator, and ascorbic acid; wherein the cAMP production promoter is forskolin (FSK), L-858051, and/or DB-cAMP in an amount within a range of 5 μM to 50 μM; wherein the BDNF signaling pathway activator is brain-derived neurotrophic factor (BDNF) in an amount within a range of 1 ng/ml to 100 ng/ml wherein the GDNF signaling pathway activator is glial cell-derived neurotrophic factor (GDNF) in an amount within a range of 1 ng/ml to 50 ng/ml; wherein the NGF signaling pathway factor is nerve growth factor-β (NGF) in an amount within a range of 1 ng/ml to 50 ng/ml; wherein the NT-3 signaling pathway activator is neurotrophin-3 (NT-3) in an amount within a range of 1 ng/ml to 50 ng/ml; and wherein the ascorbic acid is in an amount within a range of 10 µM to 100 µM.

2. The differentiation-inducing method according to claim 1, wherein the combination for culturing in step (b) further comprises a CNTF signaling pathway activator in an amount within a range of 1 ng/ml to 100 ng/ml.

3. The differentiation-inducing method according to claim 2, wherein the BDNF signaling pathway activator is 10 to 100 ng/ml of BDNF, and the CNTF signaling pathway activator is ciliary neurotrophic factor (CNTF) at 10 to 100 ng/ml.

4. The differentiation-inducing method according to claim 1, wherein the neural crest cells are derived from an organism.

5. The differentiation-inducing method according to claim 1, wherein the neural crest cells are derived from pluripotent stem cells.

6. The differentiation-inducing method according to claim 5, comprising the step of:
before the step (a), culturing the pluripotent stem cells for 6 to 16 days in a culture medium comprising DMEM/Ham's F-12 medium, hESM, or N-2 medium in the presence of a combination of compounds selected from the group consisting of BMP signaling pathway inhibitors, TGF signaling pathway inhibitors, Wnt signaling pathway activators, FGF signaling pathway activators, and EGF signaling pathway activators so as to induce the pluripotent stem cell-derived neural crest cells; wherein the BMP signaling pathway inhibitors are dorsomorphin (DM), LDN-193189, and/or noggin in an amount within a range of 1 µM to 5 µM; wherein the TGF signaling pathway inhibitor is SB431542 hydrate (SB) in an amount within a range of 1 µM to 20 µM; wherein the Wnt signaling pathway activators are CHIR99021 (CHIR), Wnt-3a, and/or BIO in an amount within a range of 1 µM to 6 µM and; wherein the FGF signaling pathway activator is fibroblast growth factor (bFGF) in an amount within a range of 4 µM to 20 µM; and wherein the EGF signaling pathway activator is epidermal growth factor (EGF) in an amount within a range of 4 µM to 20 µM.

7. The differentiation-inducing method according to claim 5, further comprising the step of:
preculturing the pluripotent stem cells for 2 to 3 days with a culture medium comprising mTeSR1 culture medium supplemented with Y-27632 in an amount within a range of 5 µM to 20 µM.

8. The differentiation-inducing method according to claim 1, wherein the cells in the step (b) are seeded at a concentration of $2\times10^5$ cells/cm$^2$ or more.

* * * * *

UNITED STATES PATENT AND TRADEMARK OFFICE
CERTIFICATE OF CORRECTION

PATENT NO. : 11,186,821 B2
APPLICATION NO. : 15/578454
DATED : November 30, 2021
INVENTOR(S) : Kida et al.

It is certified that error appears in the above-identified patent and that said Letters Patent is hereby corrected as shown below:

In the Specification

Column 5, Line 30:
Please correct "a (beta) III tubulin (TUJ1)" to read -- β (beta) III tubulin (TUJ1) --

Signed and Sealed this
Twenty-sixth Day of April, 2022

Katherine Kelly Vidal
*Director of the United States Patent and Trademark Office*